(12) United States Patent
Sicard et al.

(10) Patent No.: US 10,588,986 B2
(45) Date of Patent: Mar. 17, 2020

(54) BIOFUNCTIONALIZED NANOPARTICLES AND USES THEREOF IN ADOPTIVE CELL THERAPY

(71) Applicants: INSERM (INSTITUT NATIONAL DE LA SANTE ET DE LA RECHERCHE MEDICALE), Paris (FR); ENS—ECOLE NORMALE SUPERIEURE DE LYON, Lyons (FR); UNIVERSITE CLAUDE BERNARD-LYON 1, Villeurbanne (FR); CENTRE NATIONAL DE LA RECHERCHE SCIENTIFIQUE (CNRS), Paris (FR); HOSPICE CIVILS DE LYON, Lyons (FR)

(72) Inventors: Antoine Sicard, Lyons (FR); Olivier Thaunat, Lyons (FR)

(73) Assignees: INSERM (INSTITUT NATIONAL DE LA SANTE ET DE LA RECHERCHE MEDICALE), Paris (FR); ENS-ECOLE NORMALE SUPERIEURE DE LYON, Lyons (FR); UNIVERSITE CLAUDE BERNARD-LYON 1, Lyons (FR); CENTRE NATIONAL DE LA RECHERCHE SCIENTIFIQUE (CNRS), Paris (FR); HOSPICE CIVILS DE LYON, Lyons (FR)

( * ) Notice: Subject to any disclaimer, the term of this patent is extended or adjusted under 35 U.S.C. 154(b) by 0 days.

(21) Appl. No.: 15/763,566

(22) PCT Filed: Sep. 27, 2016

(86) PCT No.: PCT/EP2016/072983
§ 371 (c)(1),
(2) Date: Mar. 27, 2018

(87) PCT Pub. No.: WO2017/055273
PCT Pub. Date: Apr. 6, 2017

(65) Prior Publication Data
US 2018/0280536 A1     Oct. 4, 2018

(30) Foreign Application Priority Data

Sep. 28, 2015 (EP) .................... 15306506

(51) Int. Cl.
| | | |
|---|---|---|
| A61K 47/69 | (2017.01) | |
| A61K 47/68 | (2017.01) | |
| A61K 39/12 | (2006.01) | |
| C12N 7/00 | (2006.01) | |
| A61K 39/21 | (2006.01) | |
| A61K 39/00 | (2006.01) | |
| A61K 39/39 | (2006.01) | |

(52) U.S. Cl.
CPC ........ *A61K 47/6939* (2017.08); *A61K 39/001* (2013.01); *A61K 39/12* (2013.01); *A61K 39/21* (2013.01); *A61K 39/39* (2013.01); *A61K 47/6849* (2017.08); *C12N 7/00* (2013.01); *A61K 2039/505* (2013.01); *A61K 2039/5154* (2013.01); *A61K 2039/55555* (2013.01); *A61K 2039/625* (2013.01); *C12N 2740/16034* (2013.01)

(58) Field of Classification Search
CPC ............... A61K 47/6939; A61K 39/12; A61K 47/6849; A61K 2039/505; A61K 2039/55555; A61K 2039/5154; A61K 2039/625; A61K 47/6801; A61K 47/6811; A61K 47/6929; A61K 47/6933; C12N 7/00; C12N 2740/16034
See application file for complete search history.

(56) References Cited

U.S. PATENT DOCUMENTS

| | | | | |
|---|---|---|---|---|
| 8,343,497 | B2 * | 1/2013 | Shi .................. | A61K 39/00 424/184.1 |
| 2010/0129392 | A1 * | 5/2010 | Shi .................. | A61K 39/00 424/193.1 |
| 2011/0117089 | A1 * | 5/2011 | Johnson ............. | C07K 16/2803 424/133.1 |

FOREIGN PATENT DOCUMENTS

WO    2008/115641 A9    9/2008

OTHER PUBLICATIONS

Oyewumi et al., Expert Rev Vaccines 9(9): 1095-1107 (Year: 2010).*
Lloyd et al., Protein Engineering, Design & Selection 22:159-168 (Year: 2009).*
Edwards et al., J Mol Biol. 334(1): 103-118 (Year: 2003).*
Sicard et al., Nano letters 16: 297-308 (Year: 2016).*
Becton Dickson (BD) Biosciences product catalog pp. 396 and 398 (Year: 2006).*
Zsuzsanna et al: "Modulation of immune response by combined targeting of complement receptors and low-affinity Fcgamma receptors.", Immunology Letters May 4, 2010, vol. 130, No. 1-2, pp. 66-73, May 4, 2010.
Joseph et al: "Rational HIV immunogen design to target specific germline B cell receptors.", Science (New York, N.Y.) May 10, 2013, vol. 340, No. 6133, pp. 711-716, May 10, 2013.

* cited by examiner

*Primary Examiner* — Phuong Huynh
(74) *Attorney, Agent, or Firm* — W&C IP

(57) ABSTRACT

The present invention relates to biofunctionalized nanoparticles and uses thereof in adoptive cell therapy. In particular, the present invention relates to a nanoparticle comprising an amount of at least one antigen and an amount of at least one antibody having specificity for a B cell receptor wherein the antigen and antibody are attached to the surface of the nanoparticle.

19 Claims, 18 Drawing Sheets

Specification includes a Sequence Listing.

Figure 6A:
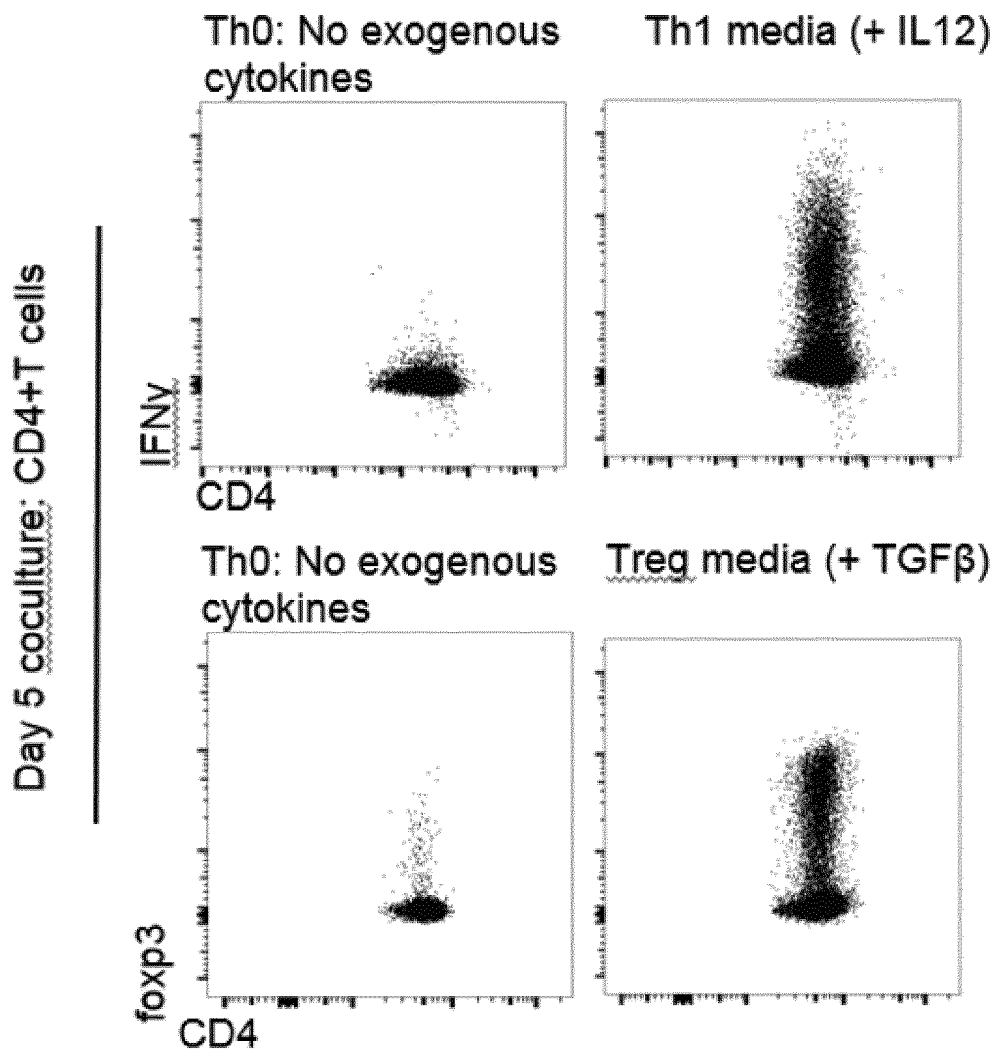
Figure 6B:
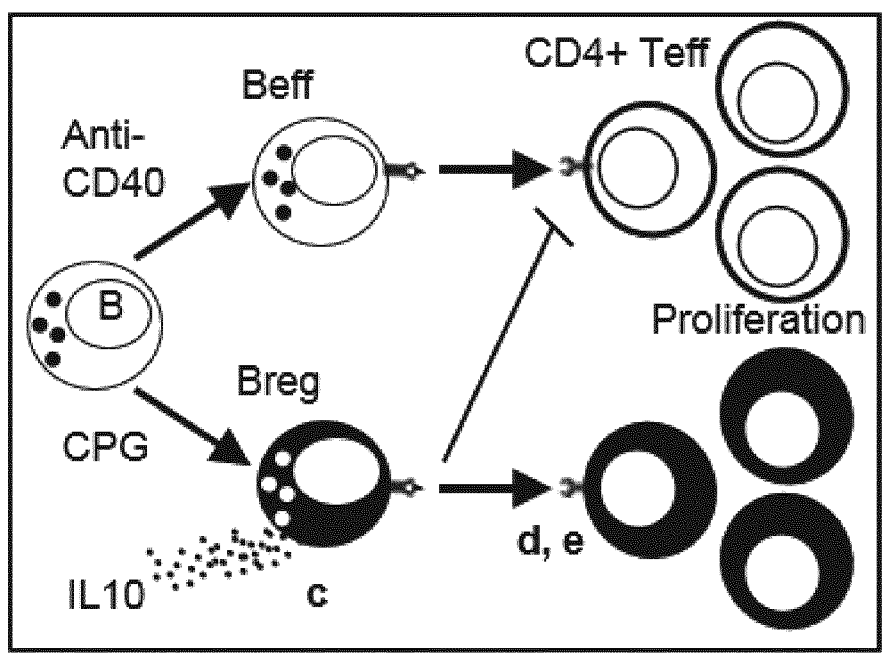
Figure 6C:
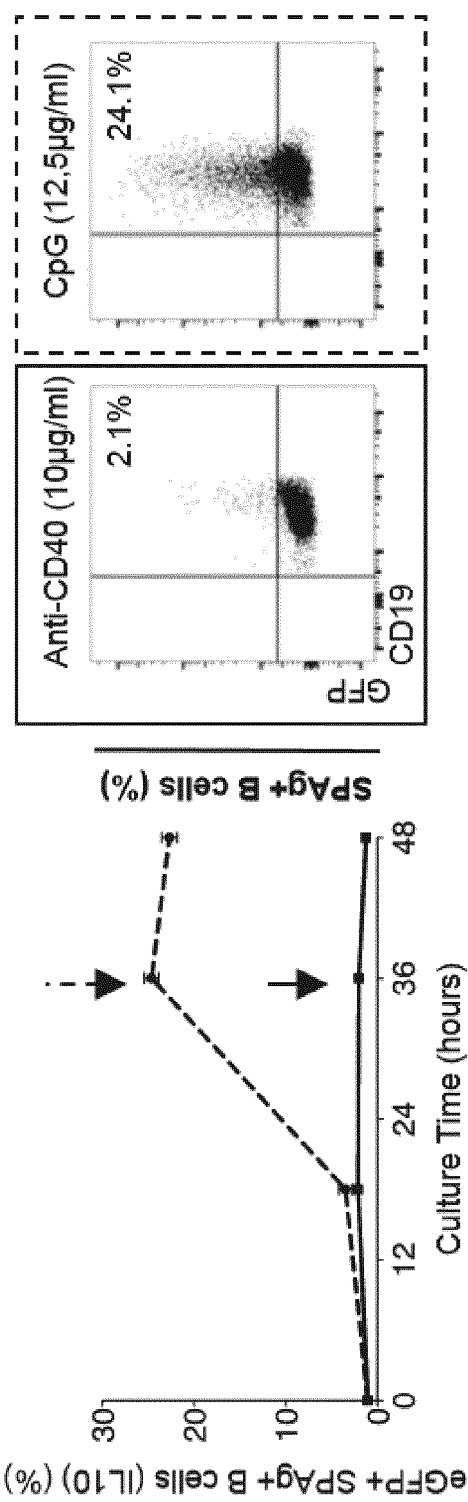
Figure 6D:
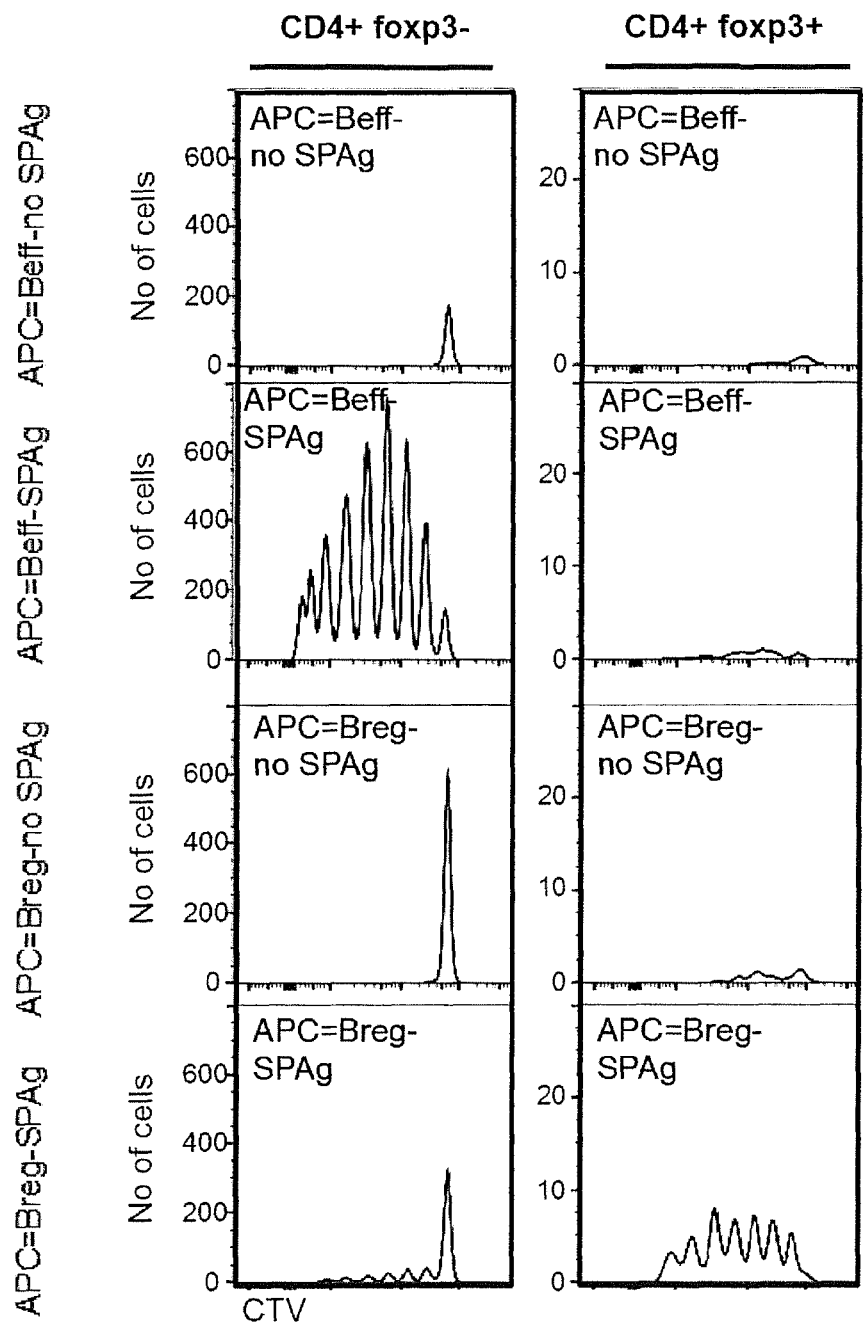

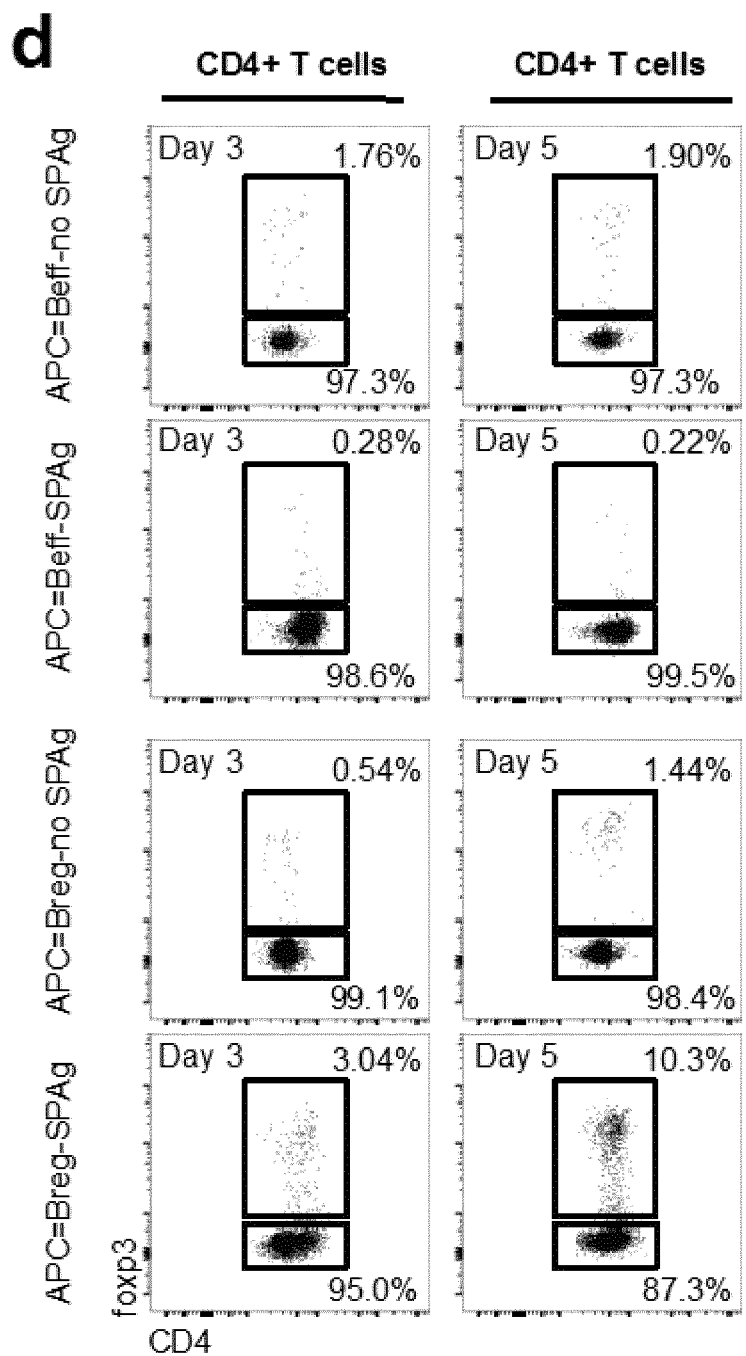
Figure 6D (first part)

BIOFUNCTIONALIZED NANOPARTICLES AND USES THEREOF IN ADOPTIVE CELL THERAPY

FIELD OF THE INVENTION

The present invention relates to biofunctionalized nanoparticles and uses thereof in adoptive cell therapy.

BACKGROUND OF THE INVENTION

For decades, immunotherapy has exclusively relied on in vivo administration of pharmacological preparations aiming at either stimulating (i.e. vaccines) or dampening (i.e. immunosuppressive drugs) patients' immune responses. Based on promising results obtained in animals models, the concept of ex vivo manipulation of immune cells for retransfer as cell therapy: "adoptive cell therapy" (ACT), has progressively emerged[1,2]. Finally, the demonstration in the late 80's that the transfer of ex vivo expanded tumor-infiltrating T lymphocytes to patients with melanoma could led to cancer regression paved the way for the translation of ACT to the clinic[3]. ACT is currently considered as a central strategy to treat severe chronic conditions as diverse as viral infections, cancers, autoimmune diseases, allograft rejection or graft versus host disease (218 trials currently registered on https://clinicaltrials.gov/).

Much of initial experimental and clinical studies in ACT have focused on cytotoxic CD8+ T cells because of their remarkable ability to kill tumors or virus-infected cells[2,4-7]. However, attention has progressively shifted to helper CD4+ T cells that are endowed with a much wider spectrum of functions[2,8,9]. CD4+ T cells are indeed: i) very efficient for tumor and viral destruction through direct cytotoxicity and promotion of cytotoxic CD8+ T cells responses[10-14], ii) necessary for the generation of protective antibody-responses[15], iii) endowed with unique immune regulatory properties in addition to their aptitudes to promote effector responses[16]. The versatility of CD4+ T cells is due to their plasticity, which allows them to polarize into various functional subsets according to the microenvironment in which they are activated[16].

Importantly, several experimental studies have illustrated that ACT was more efficient and associated with fewer side effects when antigen-specific CD4+ T cells were used instead of polyclonal CD4+ T cells[2,8,9,17]. Two recent studies have validated this concept in the clinic. First, ex vivo-expanded autologous CD4+ T-cell clones specific for a given melanoma-associated antigen were able to induce durable clinical remission in a patient with refractory metastatic melanoma[18]. Second, adoptive transfer of CD4+ T cells recognizing a unique tumor epitope could mediate regression of a metastatic epithelial cancer[19]. Such antigen-specific CD4+ T cells are however rare and need to be specifically expanded for ACT[20]. Nanobiotechnology represents a powerful tool to reach this crucial objective[21-28].

Physiologically, clonal expansion of antigen-specific CD4+ T cells requires engagement of the T cell antigen-specific receptor (TCR) by the antigen-class II major histocompatibility complex (MHCII) on the surface of antigen-presenting cell (APC). Although reports have shown that it was possible to expand ex vivo antigen-specific T cells with artificial antigen presentation by cell-free substitutes, these emerging technologies still warrant preclinical and clinical validations[21,29]. Current clinical approaches aiming at expanding CD4+ T cells clones for ACT rather rely on autologous APCs that can be reliably used to confer optimal therapeutic features to T cells before infusion[18,19]. Dendritic cells (DCs) are professional APCs that can be readily pulsed with any antigens and used as stimulators of antigen-specific CD4+ T cells[30]. Yet, implementation in practice is difficult because DCs are too rare to be directly purified from peripheral blood. Instead, bone marrow or blood progenitors must be matured in culture during several days before being used as T cells activators. This procedure increases the costs and leads to inconstant yields[31-34]. Furthermore, the number of mature DCs that can be obtained from these culture is limited because mature DCs stop to divide and become less effective at presenting antigen after 2 to 3 weeks in culture (in fact, it is generally accepted that the final number of DCs cannot be expanded beyond the number of starting progenitors)[33,34]. In contrast, B cells are "ready to use" APCs, which are abundant in the circulation (up to $0.5 \times 10^6$ cells/mL) and can be further exponentially expanded in vitro without loss of antigen-presenting functions[31-33]. B cells therefore represent an unrestricted source of autologous APCs for ACT[31,32]. However, the use of B cells as stimulators of antigen-specific CD4+ T cells is made problematic due to their inability to present non-cognate antigens[35]. In contrast with DCs, which can engulf any antigen by phagocytosis, B cells can only internalized cognate antigen[36-38]. It is indeed the binding of the specific antigen to B cell's surface immunoglobulins (B cell receptor, BCR) that triggers: (i) the activation signal required for the acquisition of potent antigen-presenting functions and (ii) the antigen internalization in endosome where antigen is processed and loaded in MHCII for presentation to CD4+ T cells. Antigen-specific B cells are too rare to be used in ACT.

SUMMARY OF THE INVENTION

The present invention relates to biofunctionalized nanoparticles and uses thereof in adoptive (T and B) cell therapy. In particular, the present invention is defined by the claims.

DETAILED DESCRIPTION OF THE INVENTION

The inventors present a novel approach to expand and polarize antigen-specific T helper cells. Antigen is vectorized into the endosomal compartment of non-cognate B-lymphocytes by means of biofunctionalized nanoparticles targeting any B cell receptors. This results in B cell activation and antigen presentation by surface MHCII molecules.

Accordingly, a first object of the present invention relates to a nanoparticle comprising an amount of at least one antigen and an amount of at least one antibody having specificity for a B cell receptor wherein the antigen and antibody are attached to the surface of the nanoparticle.

As used herein, the term "nanoparticle" has its general meaning in the art and refers to a particle from 1 nm to 5000 nm, preferably from 100 to 500 nm and even more preferably from 350 to 450 nm in size. In some embodiments, the size of the particle is about 400 nm. For most nanoparticles, the size of the nanoparticles is the distance between the two most distant points in the nanoparticle. Nanoparticle size can be determined by different methods such as Dynamic Light Scattering (DLS), Small Angle X-ray Scattering (SAXS), Scanning Mobility Particle Sizer (SMPS), Scanning Electron Microscopy (SEM), Transmission Electron Microscopy (TEM) (Orts-Gil, G., K. Natte, et al. (2011), Journal of Nanoparticle Research 13(4): 1593-1604; Alexandridis, P. and B. Lindman (2000), Amphiphilic Block Copolymers: Self-Assembly and Applications, Elsevier Science; Hunter, R. J. and L. R. White (1987). Foundations of colloid science, Clarendon Press.). Due to their surface area and ability to be conjugated with a variety of molecules, nanoparticles provide a solid platform to generate antigen-specific T helper cells by the method of the present invention.

According to the invention, the nanoparticle is biocompatible. As used herein, the term "biocompatible" refers to substances that do not alter the biological functions of a viable cell (e.g. a B cell) when the nanoparticle is internalized.

The nanoparticles of the present invention may be made of different chemical nature, of different sizes, and/or of different shapes. In some embodiments, the nanoparticles can be in the form of a sphere, needle, flake, platelet, tube, fiber, cube, prism, whiskers or have an irregular shape. Preferably, the nanoparticle is a nanosphere.

In some embodiments, the nanoparticle of the present invention is a mineral nanoparticle. Among the mineral nanoparticles, one can mention metal oxides, alumina, silica, kaolin, hydroxyapatite, calcium carbonate, silicates such as micas quartz, zeolites or clays such as hectorite, laponite, montmorillonite, bentonite, smectite . . . . Mineral particles may include, but are not limited to, metal particles. Metal particles encompass particles formed exclusively with metallic alloys or metals chosen among alkaline earth metal, transitional metal, rare earth metal, and alloys thereof. In some embodiments, the metal may be aluminum, copper, cadmium, selenium, silver, gold, indium, iron, platinum, nickel, molybdenum, silicon, titanium, tungsten, antimony, palladium, zinc, tin, and alloys thereof. These metal particles may be metal organo modified nanoparticles having chemical entities grafted to their surface or having a self-assembled monolayer of compounds, such as organosulfur compounds, on their surface. In some embodiments, particles may be particles of metal oxides, such as iron oxides (FeO, Fe2O3, Fe3O4), cerium oxide (CeO), alumina (Al2O3), zirconium oxide (ZrO2), titanium oxide (TiO2), titanates (BaTiO3, Ba0.5Sr0.5TiO3, SrTiO3), indium oxide (In2O3), tin oxide (SnO2), antimony oxide (Sb2O3), magnesium oxide (MgO), calcium oxide (CaO), manganese oxides (Mn3O4, MnO2), molybdenum oxide (MoO3), silica (SiO2), zinc oxide (ZnO), yttrium oxide (Y2O3), bismuth oxychloride, Copper oxides (CuO, Cu2O). Particles may be metal carbides, nitrides, borides, sulphides and hydroxides. They can also be organo-metallic nanoparticles: they are metal or metal oxide, carbides, nitrides, borides, sulphides and hydroxides nanoparticles, coated or grafted by an organic material. Nanoparticles can be selected among metal inorganic salts: Inorganic salts include barium sulfate, calcium carbonate, calcium sulfate, calcium phosphate, magnesium hydrogen carbonate (including sugar moieties).

In some embodiments, the nanoparticle of the present invention is made of an organic polymer. Organic polymers encompass, but are not limited to, polystyrene, poly(vinyl acetate), poly(methylstyrene), poly(acrylamide), poly(acrylonitrile), poly(vinyl chloride), poly(butyl acrylate), poly(acrylic acid), copolymers of styrene and C1-C4alkyl (meth) acrylate, copolymers of styrene and acrylamide, copolymers of styrene and acrylonitrile, copolymers of styrene and vinyl acetate, copolymers of acrylamide and C1-C4 alkyl (meth) acrylates, copolymers from acrylonitrile and C1-C4 alkyl (meth)acrylate, copolymers of acrylonitrile and acrylamide, terpolymers from styrene, acrylonitrile and acrylamide, poly (methyl methacrylate), poly(ethyl methacrylate), copolymers styrene/butadiene, styrene/acrylic acid, styrene/vinylpyrrolidone and butadiene/acrylonitrile, or methoxy poly (ethylene glycol)-poly(lactide) copolymer (MPEG-PLA). In some embodiments, the nanoparticles comprises at least a core with one or more polymers of polyvinylalcohol (PVA), polyanhydrides, polyacylates, polymethacrylates, polyacylamides, cellulose, hydromellose, starch, dendrimers, polyamino acids, polyethyleneglycols, polyethyleneglycol-co-propyleneglycol, aliphatic polyesters, including poly(lactic acid (PLA), poly(glycolic acid), and their copolymers including poly(lactic-co-glycolylic)acid (PLGA), or poly(ε-caprolactone). Polymer particles can be crosslinked or not. For instance, organic particles include, but are not limited to, nylon (for example marketed by ATOCHEM), polyethylene powders (for example marketed by PLAST LABOR), poly-2-alanine powders, polyfluorinated powders such as polytetrafluoroethylene (for example marketed by DUPONT DE NEMOURS), acrylic copolymer powders (for example marketed by DOW CHEMICA), polystyrene powders (for example marketed by PRESPERESE), polyester powders, expanded microspheres in thermoplastic material (for example marketed by EXPANCEL), microballs of silicon resins (for example marketed by TOSHIBA), synthetic hydrophilic polymer powders such as polyacrylates (for example marketed by MATSUMOTO), acrylic polyamides (for example marketed by ORIS), insoluble polyurethanes (for example marketed by TOSHNU), porous microspheres of cellulose, micro- or nanoparticles of PTFE (polytetrafluoroethylene).

In some embodiment, the nanoparticles are made of polysaccharides, i.e. molecules comprising two or more monosaccharide units. Typically the polysaccharide is selected from the group consisting of dextran, pullulan, agar, alginic acid, hyaluronic acid, inulin, heparin, fucoidan, chitosan and mixtures thereof.

In some embodiments, the nanoparticles are designed to be detectable by fluorescence spectroscopy. Favorable optical properties of fluorescent moieties to be used in the practice of the present invention include high molecular absorption coefficient, high fluorescence quantum yield, and photostability. Preferred fluorescent moieties exhibit absorption and emission wavelengths in the visible (i.e., between 400 and 700 nm) or the near infra-red (i.e., between 700 and 950 nm). Selection of a particular fluorescent moiety will be governed by the nature and characteristics of the illumination and detection systems used in the diagnostic method. In vivo fluorescence imaging uses a sensitive camera to detect fluorescence emission from fluorophores in whole-body living mammals. To overcome the photon attenuation in living tissue, fluorophores with emission in the near-infrared (NIR) region are generally preferred (J. Rao et al., Curr. Opin. Biotechnol., 2007, 18: 17-25). The list of NIR probes continues to grow with the recent addition of fluorescent organic, inorganic and biological nanoparticles. Recent advances in imaging strategies and reporter techniques for in vivo fluorescence imaging include novel approaches to improve the specificity and affinity of the probes, and to modulate and amplify the signal at target sites for enhanced sensitivity. Further emerging developments are aiming to achieve high-resolution, multimodality and lifetime-based in vivo fluorescence imaging. Numerous fluorescent moieties with a wide variety of structures and characteristics are suitable for use in the practice of the present invention. Suitable fluorescent labels include, but are not limited to, quantum dots (i.e., fluorescent inorganic semiconductor nanocrystals) and fluorescent dyes such as Texas red, fluorescein isothiocyanate (FITC), phycoerythrin (PE), rhodamine, fluorescein, carbocyanine, Cy-3™ and Cy-5™ (i.e., 3- and 5-N,N'-diethyltetra-methylindodicarbocyanine, respectively), Cy5.5, Cy7, DY-630, DY-635, DY-680, and Atto 565 dyes, merocyanine, styryl dye, oxonol dye, BODIPY dye (i.e., boron dipyrromethene difluoride fluorophore), and analogues, derivatives or combinations of these molecules.

The term "antigen" ("Ag") as used herein refers to protein, peptide, nucleic acid (e.g. DNA plasmid) or tissue or cell preparations capable of eliciting a T-cell response. In some embodiments, said antigen is a protein which can be obtained by recombinant DNA technology or by purification from different tissue or cell sources. Such proteins are not limited to natural ones, but also include modified proteins or chimeric constructs, obtained for example by changing selected amino acid sequences or by fusing portions of different proteins. The skilled person in the art will be able to select the appropriate antigen, depending on the desired T-cell stimulation.

In some embodiments, the antigen is a protein or peptide coded by a DNA or other suitable nucleic acid sequence which has been introduced in cells by transfection, lentiviral or retroviral transduction, mini-gene transfer or other suitable procedures. In some embodiments, said antigen is a protein which can be obtained by recombinant DNA technology or by purification from different tissue or cell sources. Typically, said protein has a length higher than 10 amino acids, preferably higher than 15 amino acids, even more preferably higher than 20 amino acids with no theoretical upper limit. Such proteins are not limited to natural ones, but also include modified proteins or chimeric constructs, obtained for example by changing selected amino acid sequences or by fusing portions of different proteins. In some embodiments, said antigen is a synthetic peptide. Typically, said synthetic peptide is 3-40 amino acid-long, preferably 5-30 amino acid-long, even more preferably 8-20 amino acid-long. Synthetic peptides can be obtained by Fmoc biochemical procedures, large-scale multipin peptide synthesis, recombinant DNA technology or other suitable procedures. Such peptides are not limited to natural ones, but also include modified peptides, post-translationally modified peptides or chimeric peptides, obtained for example by changing or modifying selected amino acid sequences or by fusing portions of different proteins.

In some embodiments, the antigen is a viral antigen. Examples of viral Ags include but are not limited to influenza viral Ags (e.g. hemagglutinin (HA) protein, matrix 2 (M2) protein, neuraminidase), respiratory syncitial virus (RSV) Ags (e.g. fusion protein, attachment glycoprotein), polio, papillomaviral (e.g. human papilloma virus (HPV), such as an E6 protein, E7 protein, L1 protein and L2 protein), Herpes simplex, rabies virus and flavivirus viral Ags (e.g. Dengue viral Ags, West Nile viral Ags), hepatitis viral Ags including Ags from HBV and HCV, human immunodeficiency virus (HIV) Ags (e.g. gag, pol or nef), herpesvirus (such as cytomegalovirus and Epstein-Barr virus) Ags (e.g. pp65, IE1, EBNA-1, BZLF-1) and adenovirus Ags.

In some embodiments, the antigen is a bacterial antigen. Examples of bacterial Ags include but are not limited to those from *Streptococcus pneumonia, Haemophilus influenza, Staphylococcus aureus, Clostridium difficile* and enteric gram-negative pathogens including *Escherichia, Salmonella, Shigella, Yersinia, Klebsiella, Pseudomonas, Enterobacter, Serratia, Proteus, B. anthracis, C. tetani, B. pertussis, S. pyogenes, S. aureus, N. meningitidis* and *Haemophilus influenzae* type b.

In some embodiments, the antigen is a fungal or protozoal antigen. Examples include but are not limited to those from *Candida* spp., *Aspergillus* spp., *Crytococcus neoformans, Coccidiodes* spp., *Histoplasma capsulatum, Pneumocystis carinii, Paracoccidioides brasiliensis, Plasmodium falciparum, Plasmodium vivax, Plasmodium ovale*, and *Plasmodium malariae.*

In some embodiments, the antigen is a tumor-associated antigen (TAA). Examples of TAAs include, without limitation, melanoma-associated Ags (Melan-A/MART-1, MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGP) subunit expressed by many different tumors, including but not limited to ovarian tumors, testicular tumors and myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B-cell lymphoma that can generate tumor-specific immunity (attributed to idiotype-specific humoral immune response). Moreover, Ags of human T cell leukemia virus type 1 have been shown to induce specific cytotoxic T cell responses and anti-tumor immunity against the virus-induced human adult T-cell leukemia (ATL). Other leukemia Ags can equally be used.

In some embodiments, the antigen is an auto-antigen. As used herein, the term "auto-antigen" means any self-antigen arising from the own body tissues which is mistakenly recognized by the immune system as being foreign. Autoantigens comprise, but are not limited to, cellular proteins, phosphoproteins, cellular surface proteins, cellular lipids, nucleic acids, glycoproteins, including cell surface receptors. Examples of auto-antigens include but are not limited to preproinsulin (PPI), glutamic acid decarboxylase (GAD), insulinoma-associated protein 2 (IA-2), islet-specific glucose-6-phosphatase catalytic-subunit-related protein (IGRP), zinc transporter 8 (ZnT8) and chromogranin A for T1D; myeloperoxydase and proteinase 3 for granulomatosis with polyangiitis; myelin oligodendrocyte glycoprotein (MOG) and myelin basic protein (MBP) in multiple sclerosis; and gliadins in celiac disease In some embodiments, the antigen is an allergen. As used herein, the term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

In some embodiments, the antigen is a xenoantigen. As used herein, the term "xenoantigen" has its general meaning in the art and refers to an antigen that is found in more than one species.

In some embodiments, the antigen is an alloantigen. As used herein, the term "alloantigen" has its general meaning in the art and refers in the context of a tissue graft or transplant, to the nonself MHC expressed by the cells of allografted tissue that can induce an intense immune response in the recipient host and which is aimed at eliminating the transplanted cells. Examples of alloantigens include, but are not limited to HLA molecule, minor histocompatability antigens, certain tissue-specific antigens, endothelial glycoproteins such as blood group antigens, and carbohydrate determinants. In some embodiments, the antigen is thus a HLA molecule. The term "HLA" is an acronym for "human leukocyte antigen". Thus the term "HLA molecule" means any class I or class II major histocompatibility complex glycoproteins. There are 3 major MHC class I genes in HLA: HLA-A, HLA-B and HLA-C. Minor genes are MHC class I genes in HLA HLA-E, HLA-F and HLA-G. MHC class II genes include DP, DM, DOA, DOB, DQ, and DR antigen. HLA molecules and fragments thereof can easily be produced using recombinant technology. One of skill in the art will appreciate that many different techniques are available to produce and purify recombinant proteins such as HLA molecules. For example, which is not meant to be limiting, any of the techniques listed and described in Molecular Cloning: A Laboratory Manual (Sambrook, J. and Russell, D. W., CSHL Press, Cold Spring Harbor, N.Y., 3r Edition, 2001) can be readily used to produce recombinant protein for the purposes of this invention.

In some embodiments, the antigen is a molecule that is exogenously administered for therapeutic or other purposes and may trigger an unwanted immune response. While frequently neutralising the biological activity that said molecules are meant to induce, such immune responses may have additional deleterious effects unrelated to the purpose for which the molecules were originally administered. Examples of this kind include immune reactions against therapeutic clotting factor VIII in haemophilia A or factor IX in haemophilia B, against different enzymes in congenital enzymopathies and, more in general, during any kind of replacement therapies in the context of genetic deficiencies. Allo-immunization responses against antigens expressed by tissues or hematopoietic and/or blood cells transplanted into an individual are equally considered.

The term "immunoglobulins" relates to proteins of the immunoglobulin superfamily, preferably to antigen receptors such as antibodies or B cell receptors (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, CL (constant light chain) domain, and the CH (constant heavy chain) domains CH1, CH2, CH3, and CH4. There are five types of mammalian immunoglobulin heavy chains, i.e., α, δ, ε, γ, and µ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "B cell receptor" or "BCR" refers to the antigen receptor at the plasma membrane of B cells. The B cell receptor is generally composed of a surface bound IgM or IgD antibody associated with Ig-a and Ig-β heterodimers which are capable of signal transduction. The term "transmembrane domain of a B cell receptor" preferably refers to the transmembrane domain of the antibody part of the B cell receptor, i.e., the transmembrane domain of the IgM or IgD heavy chain. In the context of the present invention, the term "B cell receptor" or "BCR" preferably refers to a mature BCR and preferably excludes the pre-BCR which comprises a surrogate light chain.

As used herein, the term "specificity" refers to the ability of an antibody to detectably bind the TCR of the present invention, while having relatively little detectable reactivity with other TCR. Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules. The term "affinity", as used herein, means the strength of the binding of an antibody to an epitope. The affinity of an antibody is given by the dissociation constant Kd, defined as $[Ab] \times [Ag]/[Ab-Ag]$, where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of antibodies is the use of Biacore instruments.

In some embodiments, the antibody of the present invention has specificity for the framework region of a kappa or lambda BCR light chain. In some embodiments, the antibody of the present invention has specificity for a framework region of a BCR heavy chain.

In some embodiments, at least 2 or 3 anti-BCR antibodies are attached to the nanoparticles. In some embodiments, at least one anti-BCR antibody having specificity for the framework region of a kappa BCR light chain and at least one anti-BCR antibody having specificity for the framework region of a lambda BCR light chain are attached to the nanoparticles. In some embodiments, at least one anti-BCR antibody having specificity for the framework region of BCR heavy chain is attached to the nanoparticles.

In some embodiments, the antibody of the present invention is a monoclonal antibody. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e. polypeptides of the present invention). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

In some embodiments, the antibody is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®".

In some embodiments, the antibody is a F(ab')2 fragment, which is a bivalent fragment comprising two Fab fragments linked by a disulfide bridge at the hinge region. These can be generated by, e.g., treating a full-length antibody with pepsin.

The antigen and the antibody of the present invention are attached to the surface of the nanoparticle by any conventional method well known in the art. For example, the attachment may involve chemical or biochemical techniques. Typically, the nanoparticle is conjugated to an avidin moiety that can create an avidin-biotin complex with the biotinylated antigens and antibodies. The term "biotinylated" as used herein, refer to any covalent or non-covalent adduct of biotin with other moieties such as the antibody or the antigen of the present invention. As used herein the term "avidin" comprises the native egg-white glycoprotein avidin, as well as any derivatives, analogs and other non-native forms of avidin that can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". As used herein, the term "biotin-avidin complex" and its variants refers to a specific linkage formed between a biotin moiety and an avidin moiety. Typically, a biotin moiety can bind with high affinity to an avidin moiety, with a dissociation constant Kd typically in the order of $10^{-14}$ to $10^{-15}$ mol/L. Typically, such binding occurs via non-covalent interactions. In some embodiments, the antigen and the antibody is monobiotinylated, i.e., is conjugated to only on biotin moiety.

The nanoparticles of the present invention are particularly suitable for preparing a population of B cells as antigen-presenting B cells.

As used herein, the term "B cell" has its general meaning in the art. B cells are lymphocytes that play a large role in the humoral immune response (as opposed to the cell-mediated immune response, which is governed by T cells). Typically, the population of B cells are prepared from a PBMC. The term "PBMC" or "peripheral blood mononuclear cells" or "unfractionated PBMC", as used herein, refers to whole PBMC, i.e. to a population of white blood cells having a round nucleus, which has not been enriched for a given sub-population. Cord blood mononuclear cells are further included in this definition. Typically, the PBMC sample according to the invention has not been subjected to a selection step to contain only adherent PBMC (which consist essentially of >90% monocytes) or non-adherent PBMC (which contain T cells, B cells, natural killer (NK) cells, NK T cells and DC precursors). A PBMC sample according to the invention therefore contains lymphocytes (B cells, T cells, NK cells, NKT cells), monocytes, and precursors thereof. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art.

As used herein, the term "antigen presenting B cell" or "APC" relates to a B-cell expressing at least one of antigen on its surface by MHCII molecules. The tem encompasses the "SPAg-loaded B cells" or "B cells SPAg" of the EXAMPLE.

Accordingly a further object of the present invention relates to a method for preparing a population of B cells as a population of antigen-presenting B cells comprising i) providing an amount of nanoparticles of the present invention wherein the antigen of interest is attached to the surface of said nanoparticles, ii) incubating the population of B cells with an amount of the nanoparticles of step i) for a time sufficient for allowing internalization of the nanoparticles into the B cells and iii) isolating the B cells that present the antigen at their surface by MHCII molecules.

In some embodiments, the method for preparing the population of antigen-presenting B cells further comprises the step of conferring regulatory properties to said population of antigen-presenting B cells. Typically, regulatory properties can be conferred to B cells by stimulating them with high amounts of a TLR agonist. As used herein the term "Toll like receptor (TLR)" has its general meaning in the art and describes a member of the Toll-like receptor family of proteins or a fragment thereof that senses a microbial product and/or initiates an innate or an adaptive immune response. Toll-like receptors include TLR1, TLR2, TLR3, TLR4, TLR5, TLR6, TLR7, TLR 8, TLR9, TLR10, TR11 and TLR12. The term "agonist" as used herein in referring to a TLR activating molecule, means a molecule that activates a TLR signaling pathway. TLR agonists are well known in the art (see e.g. Baxevanis CN, Voutsas IF, Tsitsilonis OE. Toll-like receptor agonists: current status and future perspective on their utility as adjuvants in improving anticancer vaccination strategies. Immunotherapy, 2013 May; 5(5):497-511. doi: 10.2217/imt.13.24; Shaherin Basith, Balachandran Manavalan, Gwang Lee, Sang Geon Kim, Sangdun Choi Toll-like receptor modulators: a patent review (2006-2010) Expert Opinion on Therapeutic Patents June 2011, Vol. 21, No. 6, Pages 927-944; 20. Heather L. Davis Chapter 26: TLR9 Agonists for Immune Enhancement of Vaccines, New Generation Vaccines, Fourth Edition; Jory R Baldridge, Patrick McGowan, Jay T Evans, Christopher Cluff, Sally Mossman, David Johnson, David Persing Taking a Toll on human disease: Toll-like receptor 4 agonists as vaccine adjuvants and monotherapeutic agents Expert Opinion on Biological Therapy July 2004, Vol. 4, No. 7, Pages 1129-1138.). Typically, said TLR agonist is CpG.

The antigen-presenting B cells of the present invention are particularly suitable for expanding a population of antigen-specific T helper cells.

Accordingly, a further object of the present invention relates to a method for expanding a population of antigen-specific T helper cells comprising i) providing a population of antigen-presenting B cells of the present invention specific for the antigen of interest and ii) culturing a population of T cells in the presence of the population of the antigen presenting B cells of step i).

In some embodiments, the population of T cells is isolated from a subject. The T-cells may be part of a mixed cell population isolated from the subject, such as a population of peripheral blood lymphocytes (PBL) or whole unfractionated blood. T cells within the PBL population.

The term "T helper cell" ("TH cell") refers to a subset of lymphocytes which complete maturation in the thymus and have various roles in the immune system, including the identification of specific foreign antigens in the body and the activation and deactivation of other immune cells. By this, T helper cells are involved in almost all adaptive immune responses. Mature TH cells are believed to always express the surface protein CD4 and are therefore also termed CD4+ T cells.

In some embodiments, the method further comprises the step of isolating the antigen-specific T helper cells. Methods for isolating the population of antigen-specific T helper cells are known to the skilled person. In some embodiments, the method may use HLA Class I or Class II multimers. With this procedure, Ag-reactive T cells recognizing specific peptide epitopes are detected, using either commercially available reagents (e.g., ProImmune MHC Class I Pentamers, Class II Ultimers; or Immudex MHC Dextramers) or in-house generated ones, e.g., from the NIH Tetramer Facility at Emory University, USA; from Dr. S. Buus, University of Copenhagen, Denmark [Leisner et al., *PLoSOne* 3:e1678, 2008], from Dr. G. T. Nepom, Benaroya Research Institute, Seattle, USA [Novak et al., *J. Clin. Invest.* 104:R63, 1999]. In some embodiments, the method is based on the detection of the upregulation of activation markers (e.g., CD25). With this procedure, Antigen-specific T helper cell responses are detected by their differential expression of activation markers exposed on the membrane following Ag-recognition. In some embodiments, the method may consist in a cytokine capture assay. This system developed by Miltenyi Biotech is a valid alternative to the ELISpot to visualize Antigen-specific T helper cells according to their cytokine response. In some embodiments, the method may consist of a CD154 assay. This procedure has been described in detail [Chattopadhyay et al., *Nat. Med.* 11:1113, 2005; Frentsch et al., *Nat. Med.* 11: 1118, 2005]. It is limited to detection of Ag-specific CD4+ T cells. In some embodiments, the method may consist in a CFSE dilution assay. This procedure detects Antigen-specific T helper cells according to their proliferation following Ag recognition [Mannering et al., *J. Immunol. Methods* 283:173, 2003]. Other methods suitable for detecting cell proliferation (e.g. BrdU incorporation, Ki67 expression) may also be used. Besides being suitable for detecting Antigen-specific T helper cells, said methods allows the direct sorting and/or cloning of the T cells of interest (see below).

In some embodiments, the method for the preparation of the population of antigen-specific T helper cells further comprises a step consisting of polarizing said population of antigen-specific T helper cells into a population of antigen-specific Th1 or Th2 or Th17 cells.

As used herein, the term "Th1 cell", "Th2 cell", "Th17" mean a type-1 helper T cell, a type-2 helper T cell, or a type-17 helper T cell respectively. For instance Th1 cells produce high levels of the proinflammatory cytokine IFNγ. Polarization in said T cell subset can be carried out by any conventional method well known in the art that typically consists in incubation the T cells with at least one cytokine (e.g. IL12 for Th1 cells).

In some embodiments, the method for the preparation of the population of antigen-specific T helper cells further comprises a step consisting of polarizing said population of antigen-specific T helper cells into a population of antigen-specific regulatory cells.

As used herein, the term 'Treg' or 'T regulatory cell' denotes a T lymphocyte endowed with a given antigen specificity imprinted by the TCR it expresses and with regulatory properties defined by the ability to suppress the response of conventional T lymphocytes or other immune cells. Such responses are known in the art and include, but are not limited to, cytotoxic activity against antigen-presenting target cells and secretion of different cytokines. Different types of Tregs exist and include, but are not limited to: inducible and thymic-derived Tregs, as characterized by different phenotypes such as CD4+CD25+/high, CD4+CD25+/highCD127−/low alone or in combination with additional markers that include, but are not limited to, FoxP3, neuropilin-1 (CD304), glucocorticoid-induced TNFR-related protein (GITR), cytotoxic T-lymphocyte-associated protein 4 (CTLA-4, CD152); T regulatory type 1 cells; T helper 3 cells. All these Tregs can be transformed either upon direct ex vivo purification or upon in vitro expansion or differentiation from the population of antigen-specific T helper cells of the present invention. Examples of in vitro amplification protocols can be found in Battaglia et al., J. Immunol. 177:8338-8347 (2006), Putnam et al., Diabetes 58:652-662 (2009), Gregori et al., Blood 116:935-944 (2009).

Typically, the polarization consists in incubating the antigen-specific T helper cells with an amount of at least one cytokine such as TGFbeta.

Alternatively, a population of antigen-specific regulatory cells can be prepared directly by culturing a population of T cells in the presence of the population of the antigen presenting B cells for which regulatory properties was conferred as described above (Lampropoulou, V.; Calderon-Gomez, E.; Roch, T.; Neves, P.; Shen, P.; Stervbo, U.; Boudinot, P.; Anderton, S. M.; Fillatreau, S. Suppressive functions of activated B cells in autoimmune diseases reveal the dual roles of Toll-like receptors in immunity. Immunol. Rev. 2010, 233 (1), 146-161.) (Lampropoulou, V.; Hoehlig, K.; Roch, T.; Neves, P.; Gomez, E. C.; Sweenie, C. H.; Hao, Y.; Freitas, A. A.; Steinhoff, U.; Anderton, S. M.; et al. TLR-Activated B Cells Suppress T Cell-Mediated Autoimmunity. J. Immunol. 2008, 180 (7), 4763-4773).

Alternatively, a population of antigen-specific effector cells can be prepared directly by culturing a population of T cells in the presence of the population of the antigen presenting B cells for which effector properties was conferred (Th1, Th2, Th17, Tfh).

B cells loaded with biofunctionalized nanoparticles of the invention can be used in the identification and/or purification of rare antigen-specific T cells.

The population of antigen-presenting B cells, the population of antigen-specific T cells and the nanoparticles of the present invention are particularly suitable for adoptive cell therapy in subjects in need thereof.

For example, the population of antigen-presenting B cells, the population of antigen-specific T cells and the nanoparticles of the present invention are suitable for the treatment of cancer. As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, oesophagus, gastrointestinal tract, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the population of antigen-presenting B cells, the population of antigen-specific T cells and the nanoparticles of the present invention are suitable for treating subjects afflicted with, or at risk of developing, an infectious disease, including but not limited to viral, retroviral, bacterial, and protozoal infections, etc. Subjects that can be treated include immunodeficient patients afflicted with a viral infection, including but not limited to CMV, EBV, adenovirus, BK polyomavirus infections in transplant patients, etc. Typically, the subjects at risk of developing an infectious disease include patients undergoing hematopoietic stem cell transplantation using peripheral blood or CB precursors. As used herein, the term "patient undergoing hematopoietic stem cell transplantation (HSCT)" refers to a human being who has to be transplanted with HSC graft. Typically, said patient is affected with a disorder which can be cured by HSCT. In some embodiments, the patient undergoing HSCT is affected with a disorder selected from the group consisting of leukemia, lymphoma, myeloproliferative disorders, myelodysplastic syndrome (MDS), bone marrow (BM) failure syndromes, congenital immunodeficiencies, enzyme deficiencies and hemoglobinopathies. In some embodiments, the HSCT is an allogeneic HSCT. As used herein, the term "allogeneic" refers to HSC deriving from, originating in, or being members of the same species, where the members are genetically related or genetically unrelated but genetically similar. An "allogeneic transplant" refers to transfer of cells or organs from a donor to a recipient, where the recipient is the same species as the donor. Allogeneic transplantation involves infusion of donor stem cells, typically using a donor that matches the recipient's MHC. However, matched unrelated donor (MUD) transplants are also associated with a stronger graft versus host reaction, and thus result in higher mortality rates. In another embodiment, the HSCT is an autologous HSCT. As used herein, the term "autologous" refers to deriving from or originating in the same subject or patient. An "autologous transplant" refers to collection and retransplant of a subject's own cells or organs. Autologous transplantation involves infusion of a recipient's own cells following myeloablative treatment. Autologous cell transplants minimize the risk of graft versus host disease (GVHD) and result in reduced complications. Thus, the population of antigen-presenting B cells and the population of antigen-specific T cells of the present invention are particularly suitable for preventing bacterial, viral, protozoal and/or fungal infection following CB HSCT. Non-limiting examples of viral infections include Herpes simplex virus (HSV) infections, CMV infections, Varicella-zoster virus (VZV) infections, Human herpes virus 6 (HHV6) infections, EBV infections, respiratory virus infections (such as respiratory syncytial virus (RSV), parainfluenza virus, rhinovirus, and influenza virus) and adenovirus infections. Non-limiting examples of bacterial infections include Gram-negative bacteria infections such as *Escherichia* (e.g. *Escherichia coli*), *Salmonella, Shigella*, and other Enterobacteriaceae, *Pseudomonas* (e.g. *Pseudomonas aeruginosa*), *Moraxella, Helicobacter*, and *Legionella* infections. Non-limiting examples of protozoal infections include *Giardia* infections (e.g. *Giardia lamblia*),

*Entamoeba* infections (e.g. *Entamoeba histolytica*) and *Toxoplasma* (e.g. *Toxoplasma gondii*). Non-limiting examples of fungal infections include *Aspergillus* infection (e.g. *Aspergillus fumigatus*), *Candida* infection (e.g. *Candida albicans* and non-*albicans Candida*) and other emerging fungal infections including *Trichosporon, Alternaria, Fusarium*, and Mucorales infections.

In some embodiments, the population of antigen-presenting B cells, the population of antigen-specific T cells and the nanoparticles of the present invention having regulatory properties are suitable for the treatment of autoimmune diseases. As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system, in concert with cells of the innate immune system, responds to self-antigens and mediates cell and tissue damage. In some embodiments, autoimmune diseases are characterized as being a result of, at least in part, a humoral and/or cellular immune response. Examples of autoimmune disease include, without limitation, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal and neuronal neuropathies, Behcet's disease, bullous pemphigoid, autoimmune cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), autoimmune neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, post-myocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis [Granulomatosis with Polyangiitis (GPA)]. In some embodiments, the autoimmune disease is selected from the group consisting of rheumatoid arthritis, type 1 diabetes, systemic lupus erythematosus (lupus or SLE), myasthenia gravis, multiple sclerosis, scleroderma, Addison's Disease, bullous pemphigoid, pemphigus vulgaris, Guillain-Barré syndrome, Sjogren syndrome, dermatomyositis, thrombotic thrombocytopenic purpura, hypergammaglobulinemia, monoclonal gammopathy of undetermined significance (MGUS), Waldenstrom's macroglobulinemia (WM), chronic inflammatory demyelinating polyradiculoneuropathy (CIDP), Hashimoto's Encephalopathy (HE), Hashimoto's Thyroiditis, Graves' Disease, Wegener's Granulomatosis [Granulomatosis with Polyangiitis (GPA)]. In some embodiments, the autoimmune disease is type 1 diabetes.

In some embodiments, the population of antigen-presenting B cells, the population of antigen-specific T cells and the nanoparticles of the present invention having regulatory properties are suitable for the treatment of allergies. As used herein, the term "allergy" generally refers to an inappropriate immune response characterized by inflammation and includes, without limitation, food allergies, respiratory allergies and other allergies causing or with the potential to cause a systemic response such as, by way of example, Quincke's oedema and anaphylaxis. The term encompasses allergy, allergic disease, hypersensitive associated disease or respiratory disease associated with airway inflammation, such as asthma or allergic rhinitis. In some embodiments, the method of the present invention is effective in preventing, treating or alleviating one or more symptoms related to anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD). Hypersensitivity associated diseases or disorders that may be treated by the method of the present invention include, but are not limited to, anaphylaxis, drug reactions, skin allergy, eczema, allergic rhinitis, urticaria, atopic dermatitis, dry eye disease

[or otherwise referred to as Keratoconjunctivitis sicca (KCS), also called keratitis sicca, xerophthalmia], allergic contact allergy, food allergy, allergic conjunctivitis, insect venom allergy and respiratory diseases associated with airway inflammation, for example, IgE mediated asthma and non-IgE mediated asthma. The respiratory diseases associated with airway inflammation may include, but are not limited to, rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD).

In some embodiments, the population antigen-presenting B cells, the population of antigen-specific T cells and the nanoparticles of the present invention having regulatory properties are suitable for the treatment of immune reactions against molecules that are exogenously administered for therapeutic or other purposes and may trigger an unwanted immune response. Non-limiting examples of this kind include immune reactions against replacement therapeutics in the context of genetic deficiencies, which include, but are not limited to, haemophilia A, haemophilia B, congenital deficiency of other clotting factors such as factor II, prothrombin and fibrinogen, primary immunodeficiencies (e.g. severe combined immunodeficiency, X-linked agammaglobulinemia, IgA deficiency), primary hormone deficiencies such as growth hormone deficiency and leptin deficiency, congenital enzymopathies and metabolic disorders such as disorders of carbohydrate metabolism (e.g. sucrose-isomaltase deficiency, glycogen storage diseases), disorders of amino acid metabolism (e.g. phenylketonuria, maple syrup urine disease, glutaric acidemia type 1), urea cycle disorders (e.g. carbamoyl phosphate synthetase I deficiency), disorders of organic acid metabolism (e.g. alcaptonuria, 2-hydroxyglutaric acidurias), disorders of fatty acid oxidation and mitochondrial metabolism (e.g. medium-chain acyl-coenzyme A dehydrogenase deficiency), disorders of porphyrin metabolism (e.g. porphyrias), disorders of purine or pyrimidine metabolism (e.g. Lesch-Nyhan syndrome), disorders of steroid metabolism (e.g. lipoid congenital adrenal hyperplasia, congenital adrenal hyperplasia), disorders of mitochondrial function (e.g. Kearns-Sayre syndrome), disorders of peroxisomal function (e.g. Zellweger syndrome), lysosomal storage disorders (e.g. Gaucher's disease, Niemann Pick disease). In the case of genetic deficiencies, the proposed method may not only allow to reinstate immune tolerance against the replacement therapeutics that are used to treat the disease, but also reinstate the biological activity for which said therapeutics are administered. Other therapeutics for which said method may be suitable to limit undesired immune responses include other biological agents such as, by way of example, cytokines, monoclonal antibodies, receptor antagonists, soluble receptors, hormones or hormone analogues, coagulation factors, enzymes, bacterial or viral proteins. For example, hemophilic children can be treated prophylactically with periodic coagulation factor (e.g. factor VIII) replacement therapy, which decreases the chance of a fatal bleed due to injury. In addition to the expense and inconvenience of such treatment, repeated administration results in inhibitor antibody formation in some patients against the coagulation factor. If the antibodies in these patients are low titer antibodies, patients are treated with larger doses of blood coagulation factors. If the antibodies are high titer antibodies, treatment regimens for these patients become much more complex and expensive. In some embodiments, the therapeutic protein is produced in the subject following gene therapy suitable e.g. for the treatment of congenital deficiencies. Gene therapy typically involves the genetic manipulation of genes responsible for disease. One possible approach for patients, like those with hemophilia deficient for a single functional protein, is the transmission of genetic material encoding the protein of therapeutic interest. However, the repeated administration of gene therapy vectors, such as viral vectors, may also trigger unwanted immune responses against the therapeutic protein introduced in the vector and/or against other components of the vector. Thus, the population antigen-presenting B cells and the population of antigen-specific T cells of the present invention can be suitable for overcoming the body's immune response to gene therapy vectors such as viral vectors. Viral vectors are indeed the most likely to induce an immune response, especially those, like adenovirus and adeno-associated virus (AAV), which express immunogenic epitopes within the organism. Various viral vectors are used for gene therapy, including, but not limited to, retroviruses for X-linked severe combined immunodeficiency (X-SCID); adenoviruses for various cancers; adeno-associated viruses (AAVs) to treat muscle and eye diseases; lentivirus, herpes simplex virus and other suitable means known in the art.

In some embodiments, the population antigen-presenting B cells, the population of antigen-specific T cells and the nanoparticles of the present invention having regulatory properties are suitable for the treatment of immune reactions against a grafted tissue or grafted hematopoietic cells or grafted blood cells. Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the present invention is also particularly suitable for preventing or suppressing an immune response associated with rejection of a donor tissue, cell, graft, or organ transplant by a recipient subject. Graft-related diseases or disorders include graft versus host disease (GVHD), such as associated with bone marrow transplantation, and immune disorders resulting from or associated with rejection of organ, tissue, or cell graft transplantation (e.g., tissue or cell allografts or xenografts), including e.g., grafts of skin, muscle, neurons, islets, organs, parenchymal cells of the liver, etc. Thus the method of the invention is useful for preventing Host-Versus-Graft-Disease (HVGD) and Graft-Versus-Host-Disease (GVHD). The chimeric construct may be administered to the subject before, during and/or after transplantation (e.g., at least one day before transplantation, at least one day after transplantation, and/or during the transplantation procedure itself). In some embodiments, the chimeric construct may be administered to the subject on a periodic basis before and/or after transplantation.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., daily, weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The population of antigen-presenting B cells and the population of antigen-specific T cells of the present invention can be utilized in methods and compositions for adoptive cell therapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the Antigen-specific T helper cells with the desired specificity, on the age and weight of the recipient, on the severity of the targeted condition and on the immunogenicity of the targeted Ags. These amount of cells can be as low as approximately 103/kg, preferably 5×103/kg; and as high as 107/kg, preferably 108/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

As used herein, the term "administering" refers to administration of the compounds as needed to achieve the desired effect. Administration may include, but is not limited to, oral, sublingual, intramuscular, subcutaneous, intravenous, transdermal, topical, parenteral, buccal, rectal, and via injection, inhalation, and implants.

The invention will be further illustrated by the following figures and examples. However, these examples and figures should not be interpreted in any way as limiting the scope of the present invention.

FIGURES

FIG. 1. Biofunctionnalization of nanospheres to generate synthetic particulate antigens (SPAg).

(a) Schematic representation of the system used to vectorize chosen antigen into non-cognate B cell: 400 nm fluorescent streptavidin-coated nanospheres are decorated with biotinylated-antigens and biotinylated-monoclonal antibody (mAb) directed against a framework region of B cell receptor's kappa light chains (anti-κ mAb).

(b) (Top) Verification of nanospheres coating with anti-κ mAb by electron microscopy (EM) using gold particle-coupled anti-IgG secondary antibody. (Bottom) Coating efficiency using biotinylated (bonds; black histogram) versus purified (adsorption; grey histogram) anti-K mAb was compared in flow cytometry using a PE-conjugated anti-IgG secondary antibody.

(c) Verification of double coating with biotinylated-anti-κ mAb and antigen (ovalbumin) by flow cytometry.

(d, left) Impact of polybiotinylation (blue histogram) vs monobiotinylation (orange histogram) of the proteins used for coating on nanospheres flocculation assessed by flow cytometry analysis of the particle size (The Forward-Scattered Light parameter (FSC) is proportional to the size of the analyzed event).

(d, right) After coating of nanospheres with mono-biotinylated proteins, aggregates were excluded by filtration through a low-binding membrane with a pore size of 650 nm. Histogramms and representative images of the SPAg fluorescence analyzed by imaging flow cytometry in the upper (orange) and lower (red) chambers of centrifugal devices.

(e) Estimation of the number of antigen molecules coated on each nanosphere by the saturation curve method. Nanospheres were incubated with increasing amounts of biotinylated ovalbumin. Ovalbumin binding was measured by flow cytometry with a FITC-conjugated anti-ovalbumin mAb.

(f) Numeration of SPAg by spectrophotometry using the standard curve method. Uncoated nanospheres samples of known concentrations are used as standards.

FIG. 2. SPAg behave like genuine particulate antigen.

(a) Scheme representing the first steps of B cell activation by a particulate antigen. The binding of cognate epitope to B cell receptors (BCR) provides the first signal of activation (signal 1) to B cells and leads to the internalization of the antigen in the endosomal compartment where the antigen is then processed and loaded onto MHC class II molecules.

(b) B cells from wild type mice were incubated 10 minutes at 4° C. with SPAg and washed. (Left) Flow cytometry dot plots showing SPAg fluorescence according to B220 and lambda-chain expression. (Upper right) Flow cytometry dot plots showing the percentages of follicular (FO: $CD21^{int}CD23^{high}$) and marginal zone (MZ: $CD21^{high}CD23^{low}$) subsets among kappa positive B cells without (left, blue) and with (right, red) SPAg. (Lower right) EM images of B cells without (left, blue) or with (right, red) SPAg bound to their surface.

(c) SPAg triggers BCR signalling cascade. B cells from wild type mice were incubated 1, 2 or 3 minutes at 37° C. with either anti-IgM soluble Fab'2 (positive control) or SPAg. Imaging flow cytometer was used to detect the phosphorylated form of the B cell linker protein (p-BLNK). (Left) Representative images showing p-BLNK staining in lambda positive and lambda negative B220+ B cells after anti-IgM (upper) or SPAg (lower) stimulation. (Right) The percentage of SPAg that have triggered BCR signalling at 1, 2 and 3 minutes is shown.

B cells from wild type mice were incubated 10 minutes at 37° C. with SPAg.

(d) Kinetic of SPAg internalization was defined using Image flow cytometer. (Upper) B cells were incubated at various time points with a fluorescent anti-ovalbumin mab, only non-internalized SPAg were accessible to the staining. (Lower) The percentages of SPAg internalized (red) and bound to B cell surface (green) is shown at various time points.

FIG. 3. SPAg-loaded B cells induce antigen-specific T cells activation and proliferation.

(a) Scheme representing B cell presenting the antigen to CD4+ T cell. Internalized antigen is processed in late endosomal compartment, loaded onto MHC class II molecules, and presented on B cell surface. Together with the expression of costimulation molecules (CD80/86), antigen presentation leads to activation and proliferation of cognate CD4+ T cells.

(b) SPAg-induced MHC class II and CD86 upregulation. B cells from wild type mice were incubated (red histogram) or not (black histogram) with SPAg 10 minutes at 37° C. and cultured overnight. MHC class II (upper) and CD86 (lower) expression was assessed by flow cytometry.

SPAg-loaded B cells are potent antigen-presenting cells to CD4+ T lymphocytes.

(c) Bone marrow-derived dendritic cells (BMDC) or B cells from wild type mice were incubated 4 hours with soluble ovalbumin or with SPAg before being cocultured 72 hours at a 1:1 ratio with CTV-labelled ova-specific CD4+ T cells from OTII transgenic mice. Expression of the activation marker CD25 by OTII CD4+ T cells was assessed at 72 hours by flow cytometry.

(d) OTII CD4+ T cell proliferation was measured at 72 hours by flow cytometry in the various culture conditions.

FIG. 4. SPAg-based approach is applicable in humans.

Purified B cells from a healthy volunteer were incubated 30 minutes at 37° C. with SPAg coated with anti-human kappa-light chain mAbs (hSPAg) and washed.

(a) Flow cytometry dot plots showing hSPAg fluorescence according to lambda-chain expression by B cells.

(b) Image flow cytometer was used to evaluate hSPAg internalization after 12 hours culture. (Left) Representative images showing hSPAg internalized in CD19+ B cells. (Right) Quantification of cells that have internalized hSPAg among lambda+ and kappa+ B cells.

(c) (Top) Schematic representation of the experimental procedure. Purified B cells from an HLA-DR01/01 healthy volunteer were incubated 30 minutes at 37° C. with hSPAg coated with either ovalbumin (negative control, hSPAg-ova) or a peptide made of 3 repetitions of a sequence of HIV-GAG protein (hSPAg-GAG). After washing, B cells were rested 12 hours and then coculture 6 hours with HLA-DR1-restricted CD4+ T cell clones specific for the HIV-GAG protein. Clones activation was assessed by flow-cytometry measurement of the intracellular cytokine MIP-1β. (Bottom) Flow cytometry dot plots showing hSPAg fluorescence according to lambda-chain expression by B cells (left) and MIP-1β staining in CD4+ T cells clones (right) under three different experimental conditions (clones cocultured with B cells without hSPAg, with B cells-hSPAg-ova and with B cells-hSPAg-GAG).

FIG. 5. SPAg-loaded B cells to expand rare cognate CD4+ T cells.

SPAg-loaded B cells from WT mice were cocultured 72 hours at a 1:2 ratio with a mix of cognate OTII CD4+ T cells (CD45.2) and polyclonal T cells (CD45.1). CD45.2/CD45.1 ratios were (a) 1/100, (b) 1/1000 or (c) 1/10000. (Far left) Flow cytometry analysis at 72 hours showing CD45.1 and CD45.2 staining of CD4+ T cells and (middle left) their respective proliferation profiles assessed by CTV staining. (Middle right) Bar charts representing the proportion of CD45.1 and CD45.2 CD4+ T cells that have undergone division. (Far right) CD45.2/CD45.1 ratios at the beginning (H0) and at the end (72 hours) of the coculture.

FIG. 6. SPAg-loaded B cells to polarize cognate CD4+ T cells.

(a) B cells from wild type mice were incubated with SPAg 10 minutes at 37° C., washed and cocultured 5 days at a 1:1 ratio with OTII CD4+ T cells in media without exogenous cytokines (Th0, black plots), with recombinant IL12 (Th1, red plot, 20 ng/ml) or with TGFβ (Treg, blue plot, 1 ng/ml). Flow cytometry dot plots showing IFNγ staining under Th0 and Th1 polarizing conditions (left) and Foxp3 staining under Th0 and Treg polarizing conditions (right) in CD4+ T cells at 5 days of coculture.

(b) A scheme describing how regulatory properties can be conferred to SPAg-loaded B cells. B cells are loaded with SPAg and cultured with CpG. SPAg-loaded B reg produce IL-10 (c), do not induce significant proliferation of antigen-specific Foxp3− effector T cells (Teff) but rather promote the proliferation of antigen-specific Foxp3+ regulatory T cells (Treg) (d, e).

(c) B cells from IL10-IRES-eGFP mice were incubated with SPAg 10 minutes at 37° C. and cultured 48 hours in medium supplemented with either anti-CD40 agonist (10 μg/ml; black curve) or with CpG (12.5 μg/ml; green curve). The proportion of eGFP-positive SPAg-positive B cells was measured by flow cytometry at various time points.

(d) B cells from wild type mice were incubated or not with SPAg 10 minutes at 37° C. and cultured 36 hours in medium supplemented with either anti-CD40 agonist or with CpG. B cells without SPAg and sorted SPAg-positive B cells were cocultured 5 days at a 1:1 ratio with CTV-labelled OTII CD4+ T cells. (left) The proportions of effector (Foxp3$^{neg}$) and regulatory (Foxp3$^{pos}$) CD4+ T cells were determined by flow cytometry at 3 and 5 days of coculture in the various culture conditions. (right) The proliferation profiles of effector (Foxp3$^{neg}$) and regulatory (Foxp3$^{pos}$) CD4+ T cells were determined by flow cytometry at 5 days of coculture in the various culture conditions. Data are representative of two independent experiments.

EXAMPLE 1

Material And Methods

Surrogate Particulate Antigens (SPAg)
Proteins Biotinylation
Ovalbumin (Ova, Sigma), purified rat anti-mouse κ Light Chain (anti-κ mAb, clone 187.1, Becton Dickinson (BD)) and purified mouse anti-human κ Light Chain (clone G20-361, BD) were monobiotinylated using the EZ-Link™ Sulfo-NHS-LC-LC-Biotin kit (Thermo Scientific). Briefly, proteins suspended in phosphate-buffered saline (PBS) were incubated for 30 minutes at room temperature with Sulfo-NHS-LC-LC-Biotin at a 1:1 molar ratio. Excess non-reacted biotin was eliminated with Zeba Spin Desalting Columns, 7K MWCO (Thermo Scientific). Biotin Quantitation Kit (Pierce, Thermo Scientific) was used to determine the level of biotin incorporation.

HIV-GA G Trimer Peptide

Custom monobiotinylated trimer peptide was synthetized by Lifetein. Purity was 95.82%. Sequence was: Biotin-IILGLNKIVRMYSPTSILDIRQGPK-IIL-GLNKIVRMYSPTSILDIRQGPK-IIL-GLNKIVRMYSPTSILDIRQGPK, 75aa (SEQ ID NO:1).

Coupling Procedure 400 nm flash red (660/690) streptavidin nanospheres (Bangs Laboratories) were washed two times (PBS, 1% bovine serum albumin (BSA; Sigma), 0.0005% Tween 20 (Sigma)) with 100 nm pore size Ultrafree-MC DV Centrifugal Filters (2000G/2 minutes, Durapore, Merck Millipore). Nanospheres were incubated for 30 minutes at room temperature with excess monobiotinylated-ova or monobiotinylated-trimer HIV-GAG peptide and with anti-mouse or anti-human K mAb with constant mixing.

Coated nanospheres (SPAg) were washed two times in Tween 20-free PBS-1% BSA buffer prior to filtration through 650 nm pore size Ultrafree-MC DV Centrifugal Filters (2000G/2 minutes, Durapore, Merck Millipore).

SPAg Quantification

The standard curve method was used to numerate SPAg. Briefly, SPAg samples and serial dilutions of uncoated nanospheres of known concentrations were pipetted into 96 wells black plates with transparent bottom (Greiner Bio One) to establish a standard curve. Fluorescence was measured with a microplate reader (Infinite Reader M200, Tecan) at 660/690 nm. Data were analyzed with the i.control (v1.6) and Excel softwares.

Mice

Wild type C57BL/6 (CD45.2), Ly5.1 C57BL/6 (CD45.1) and OTII TCR transgenic C57BL/6 mice aged 8-15 weeks were purchased from Charles River Laboratories (Saint Germain sur l'Arbresle, France). IL10-reporter mice (IL10-IRESeGFP) were purchased from Jackson Laboratories (Bar Harbor, Me., USA). All mice were maintained under EOPS condition in our animal facility (PBES, Lyon, France). All experimental protocols were approved by the local ethical committee (CECCAPP).

Healthy Volunteer Blood Donation

Two HIV-seronegative healthy volunteer donors provided peripheral blood after informed consent. Blood collection was organized at the Etablissement Francais du Sang, Lyon, France.

Cell Preparations and Cultures

Mouse B Cells

After spleen cells were harvested and erythrocytes lysed (ACK Lysing Buffer, Invitrogen), B cells were enriched to >95% purity by negative selection using magnetic enrichment kits (R&D system or Milteny Biotec).

Human B Cells

Peripheral Blood Mononuclear Cells (PBMC) were isolated by centrifugation on Ficoll density gradient (Histopaque, 10777, Sigma). B cells were enriched to >95% purity by negative selection using magnetic enrichment kits (R&D system).

B Cells Loading With Spag And Culture

Pre-warmed B cells were incubated with SPAg for 10, 30 minutes or 6 hours (according to the experiments) at 37° C. in 5% CO2 at a 100 SPAg to B cell ratio. After two washes, cells were cultured at 37° C. in 5% CO2, in complete media (mouse: RPMI 1640 media Glutamax (Invitrogen) supplemented with 10% FCS, 50 µM β-mercaptoethanol (Sigma), 25 mM Hepes (Invitrogen), and 10 units/mL penicillin/streptomycin (Invitrogen); humans: Yssel medium as previously described[1]). When indicated, anti-CD40 agonist (clone FGK45, 10 µg/ml; Enzo Life Sciences Inc;) or CPG (1668, 12.5 µg/ml; mWG Biotech) were added.

Bone Marrow-derived Dendritic Cells (BMDC) Preparation and Loading

Dendritic cells were generated from bone marrow of C57Bl/6 mice as described previously[2]. Briefly, bone marrow was prepared from femurs and tibiae of mice. Cells were cultured in 6 wells plates at a concentration of $10^6$ cells/ml in 4 ml complete medium supplemented with 1% culture supernatant containing GM-CSF (4 ng/ml final concentration). After 3 days, medium was removed and replaced with 4 ml of fresh medium. On days, 6 and 9, 4 ml of fresh medium was added without disrupting cells. Cells were collected on day 12, washed and resuspended in complete medium without GM-CSF. Purity was assessed by flow cytometry and was >90% (CD11c+MHC-II+ cells). BMDC were incubated with soluble ovalbumin (200 µg/ml) or with SPAg for 6 h at 37° C. in 5% CO2 before being used as stimulators in the presentation assay.

Mouse Presentation Assay

CD4+ T cells were enriched from spleens of Ly5.1 C57BL/6 (CD45.1) or OTII transgenic mice (CD45.2) to >95% purity by negative selection using magnetic enrichment kits (R&D system or Milteny Biotec). CD4+ T cells were labelled with cell trace violet according to the manufacturer's protocol (Molecular probes, Life technology) before being cocultured with B cells or BMDC at a 1:1 ratio (96 wells plates, $2.10^5$ cells per well). T cells proliferation was measured by flow cytometry at 3, 4 or 5 days.

Human Presentation Assay

Purified B cells from an HLA-DR01/01 healthy volunteer were incubated 30 minutes at 37° C. with hSPAg coated with trimeric HIV-GAG peptide. After washing, B cells were rested 12 hours in complete medium at 370 and then coculture 6 hours at a 1:1 ratio with HLA-DR01-restricted CD4+ T cell clones specific for the HIV-GAG protein. Clones were generated as previously described[3]. After one hour of coculture, monensin (Biolegend) was added to culture media. Clone activation was assessed by flow cytometry measurement of the intracellular cytokine MIP-1β at H6.

Flow Cytometry

Antibodies

In mice experiments, antibodies directed against the following targets were used: CD3 (clone 452C11, BD), CD4 (clone RM-44, BD), CD8 (clone 53-6.7, BD), CD11c (clone HL3, BD), CD19 (clone ID3, BD), CD21 (clone 7G6, BD), CD23 (clone B3B4, BD), CD25 (clone PC61, BD), CD45.1 (clone A20, BioLegend), CD45.2 (clone 104, eBiosciences), CD80 (clone 16-10A1, BD), CD86 (clone GL1, BD), B220 (clone RA3-6B2, BD), F4/80 (clone BM8, eBiosciences), lambda light-chain (clone JC5-1, Abcam), pBLNK (clone J117-1278, BD), MHC-II (clone 2G9, BD), foxp3 (clone FJK-16s, ebiosciences), rat IgG1 (clone G1 7E7, Abcam), ovalbumin (Abcam).

In human experiments, antibodies directed against the following targets were used: CD4 (clone RPA-T4, BD), DC-SIGN (clone DCN46, BD), CD19 (clone HIB19, BD), lambda light-chain (CLONE JDC-12, BD), MIP1b (Clone 24006, R&D system).

Procedures

Single cell suspensions were incubated with a blocking anti-mouse Fc receptor antibody (clone 2.4G2) to prevent non-specific antibody binding and then with relevant fluorescent monoclonal antibodies for 15 minutes at 4° C. in flow buffer (PBS-Azide 0.01%-SVF 2%-EDTA 0.5 mM). Dead cells were excluded by staining with Fixable Viability Dye (eBiosciences) or 4',6-diamidino-2-phenylindole (DAPI). For cytokine intracellular staining, cells were then fixed and permeabilized before being incubated for 30 minutes at 4° C. with the relevant antibodies. For foxp3 intranuclear staining, the mouse regulatory T Cell staining kit was used according to the manufacturer's protocol (eBiosciences).

For phosphoflow analysis, the phospho-epitopes exposure kit (Beckman Coulter) was used. Briefly, $1 \cdot 10^6$ prewarmed B cells were stimulated with either anti-IgM soluble F(ab')2 (15 µg/ml) or SPAg at 37° C. for 1, 2 or 3 minutes before being incubated 10 minutes at room temperature with fixative reagent and then 5 minutes at 37° C. with permeabilizing reagent. Before incubation with anti-lambda light chain, anti-B220 and mouse anti-pBLNK mAbs (30 minutes at room temperature), permeabilized cells were incubated for 15 minutes with kappa light-chain positive mouse IgG isotype control (clone X40, BD) in order to avoid reactivity between anti-κ mAb present on SPAg and mouse PE anti-pBLNK mAb.

Data Collection

Data were collected on LSRII or LSR Fortessa flow cytometers (BD Biosciences, San Jose, Calif., USA) and analyzed with FlowJo software (v10.0). For image analysis, samples were acquired on a 4 laser ImageStream X Mark II (Amnis-EMD Millipore) with 60× magnification and analyzed with IDEAS software (v6.0).

Electron Microscopy

Ultrastructural Analysis of B Cells

B cells were incubated 10 minutes at 37° C. with SPAg, cultured overnight and fixed in glutaraldéhyde 4% and cacodylate 0.2M. Samples were washed three times in saccharose 0.4M/0.2 M Na C—HCl-Cacodylate-HCl Ph7.4 0.2M for 1 hour at 4° C., and postfixed with 2% OsO4/0.3M Na C—HCl Cacodylate-HCl pH 7.4 for 1 hour at 4° C. Then, cells were dehydrated with an increasing ethanol gradient (5 minutes in 30%, 50%, 70%, 95%, and 3 times for 10 minutes in absolute ethanol). Impregnation was performed with Epon A (50%) plus Epon B (50%) plus DMP30 (1,7%). Inclusion was obtained by polymerisation at 60° C. for 72 hours. Ultrathin sections (approximately 70 nm thick) were cut on a Reichert ultracut E (Leica) ultramicrotome, mounted on 200 mesh copper grids coated with 1:1,000 polylisine, and stabilized for 1 day at room temperature (RT) and, contrasted with uranyl acetate and lead citrate. Sections were examined with a Jeol 1400JEM (Tokyo, Japan) transmission electron microscope equipped with a Orius 1000 camera and Digital Micrograph (CIQLE-Centre d'Imagerie Quantitative Lyon Est-Université Claude Bernard Lyon).

Verification of Nanospheres Coating with Biotinylated Rat Anti-mouse Kappa-light Chain mAb Immunogold labelling was performed by floating the grids on drops of reactive media. Nonspecific sites were coated with 1% BSA and 1% normal goat serum in 50 mM Tris-HCl, pH8.2 for 20 min at room temperature. Thereafter, incubation was carried out 45 min at room temperature in wet chamber with 10 nm gold-conjugated goat anti-rat Ab (British Bio Cell international, 1/80) in 1% BSA+50 Mm Tris-HCl pH 8.2. The immunocomplexe was successively washed three times in 50 Mm Tris-HCl pH8.2 and pH 7.4 and three times with infiltrated distilled water and fixed by a wash in glutaraldehyde 4% for 3 min. Sections were stained with 0.5% uranyl acetate in ethanol 50% for 5 min in darkness and observed with a Jeol 1400JEM (Tokyo, Japan) transmission electron microscope equipped with a Orius 1000 camera and Digital Micrograph (CIQLE-Centre d'Imagerie Quantitative Lyon Est-Université Claude Bernard Lyon).

Confocal Microscopy

B cells loaded with SPAg were cultured overnight. $1 \cdot 10^5$ B cells were plated on 17 mm glass coverslips (Zeiss) preincubated 4 hours with 0.01% poly-L-lysine (Sigma). Cells were permeabilized with 0.05% saponin, then incubated for 30 minutes at room temperature with blocking solution (PBS-5% BSA) and stained with Alexafluor488-conjugated anti-B220 (clone RA3-6B2, BD) and PE-conjugated anti-LAMP1 (clone 1D4B) mAbs for 45 minutes at room temperature. After 3 washes with PBS-5% BSA, cells were stained with DAPI (1/5000) for 10 minutes. After 3 additional washes, coverslips were mounted on glass slides with fluoromount aqueous mounting medium (Sigma). Confocal 3D image stacks were acquired with confocal spectral SP5 microscope (Leica). Images were analyzed with FIJI software.

Data Analysis

Statistical analyses and graphs were performed using Prism software (GraphPad, V6.0). Unless noted otherwise, the data are represented as mean values±SD. p values<0.05 were considered significant (Mann-Whitney test).

References (1) Yssel, H.; de Vries, J. E.; Koken, M.; Van Blitterswijk, W.; Spits, H. *J. Immunol. Methods* 1984, 72, 219-227.

(2) Lutz, M. B.; Kukutsch, N.; Ogilvie, A. L.; Rössner, S.; Koch, F.; Romani, N.; Schuler, G. *J. Immunol. Methods* 1999, 223, 77-92.

(3) Moris, A.; Pajot, A.; Blanchet, F.; Guivel-Benhassine, F.; Salcedo, M.; Schwartz, O. *Blood* 2006, 108, 1643-1651.

EXAMPLE 2

B Cells Loaded With Synthetic Particulate Antigens: A Versatile Platform To Generate Antigen-Specific Helper T Cells For Cell Therapy We have developed an innovative strategy for biofunctionalization of nanoparticles. Bioengineered nanospheres were specifically designed to simultaneously: i) provide activation signal, and ii) deliver non-cognate antigens to endosomes of B cells. Using these Synthetic Particulate Antigens (SPAg), we were able to turn resting polyclonal B cells into potent stimulators of antigen-specific CD4+ T cells.

Figure 1A:
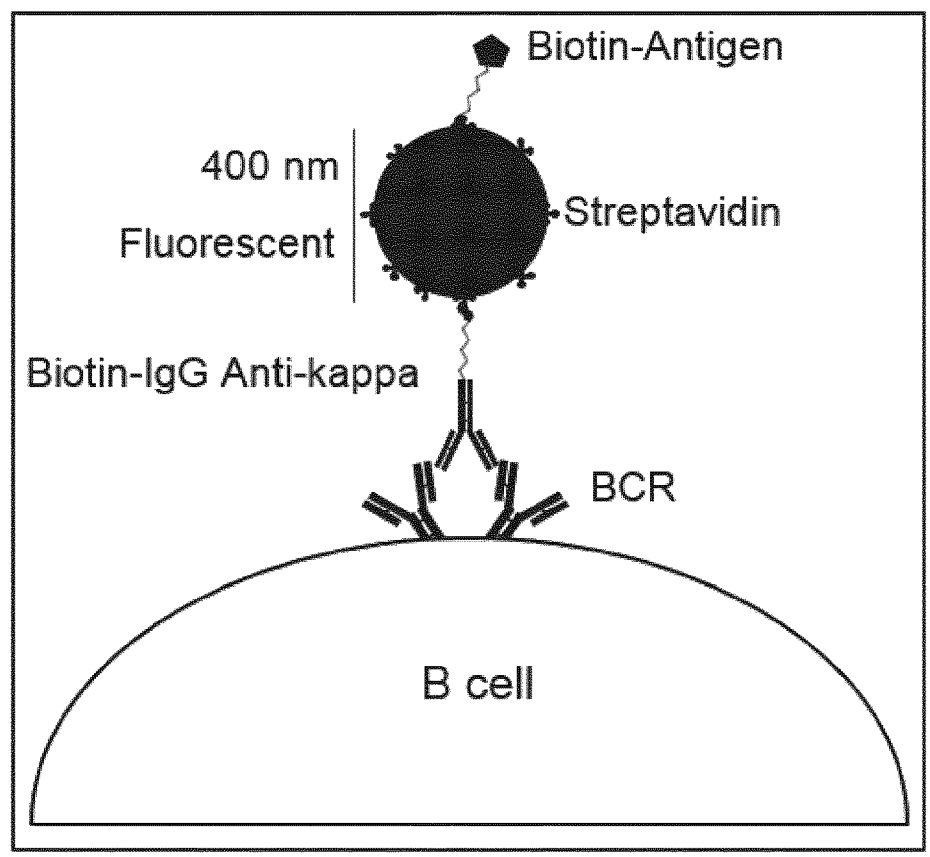
Figure 1B:
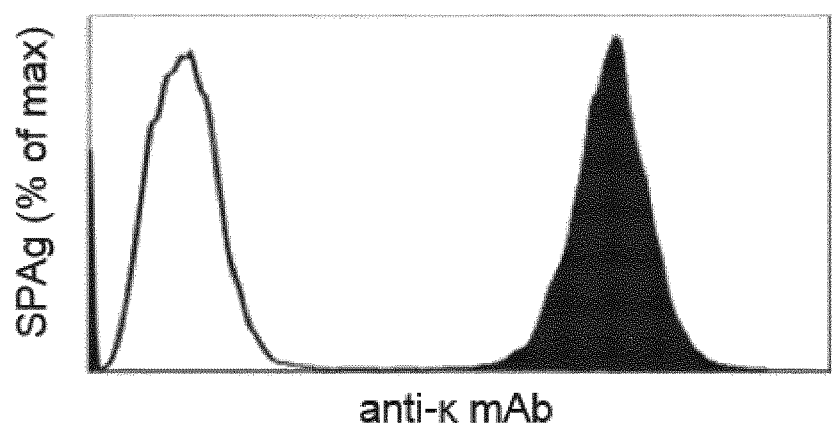
Figure 1B:
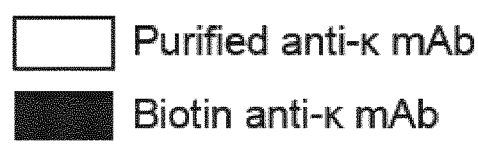
Figure 1C:
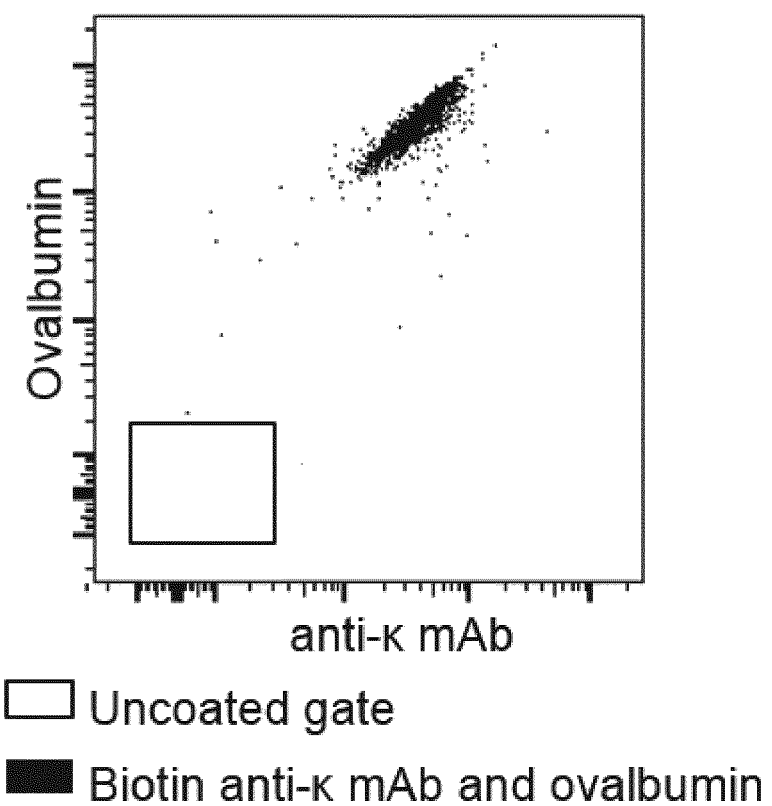
Figure 1D:
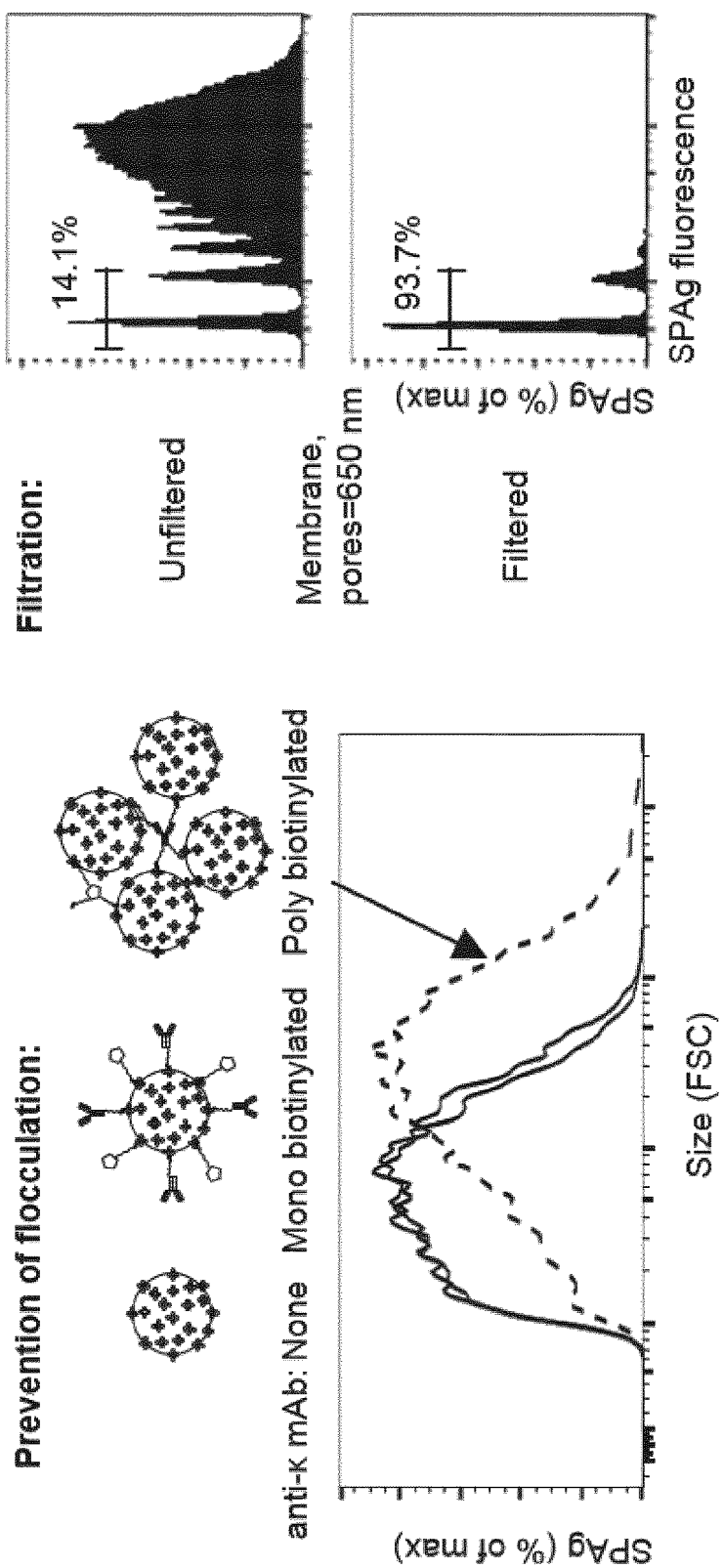
Figure 1E:
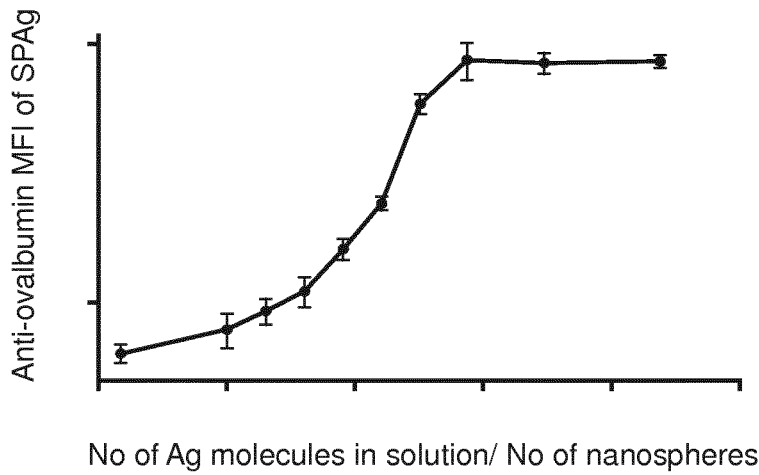
Figure 1F:
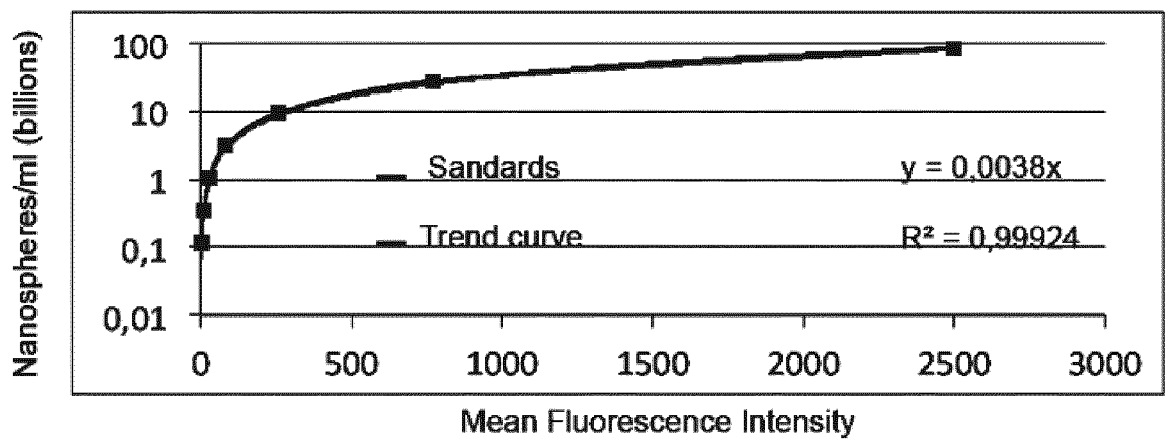

To generate SPAg, proteins of interest were biotinylated and immobilized on fluorescent streptavidin-coated nanospheres of 400 nm in diameter, a size comparable to the one of a typical pathogen which offers a good compromise between the possibility to be internalized by B cells and binding capacity[39]. BCR is composed of 2 pairs of polypeptides chains: 2 heavy chains and 2 light chains. Light chains can be of two types: lambda or kappa. More than 90% of murine B cells express kappa light chains. Each chain comprises both a constant domain, which is a shared framework independent of the antigenic specificity, and a highly variable domain, which is specific to each B cell clone and involved in the recognition of antigenic epitopes. We assumed that coating the nanospheres with a biotinylated monoclonal antibody directed against a framework region of kappa light chain (anti-κ mAb) would confer them the capacity to target any non-cognate kappa positive BCR while behaving like genuine particulate antigens (FIG. 1a). The coating of nanospheres with anti-κ mAb was verified by electron microscopy (EM) using gold particle-coupled anti-IgG secondary antibody (FIG. 1b, top). To ensure that anti-κ mAb were attached to nanospheres by streptavidin-biotin solid bonds rather than unspecific adsorption, coating efficiency using biotinylated versus purified anti-κ mAb was compared in flow cytometry with a PE-conjugated anti-IgG antibody (FIG. 1b, bottom). The successful double coating of nanospheres with biotinylated anti-κ mAb and ovalbumin, which was used herein as model antigen, was verified by flow cytometry (FIG. 1c). To limit flocculation of nanospheres caused by the coating procedure, anti-κ mAb and ovalbumin had to be monobiotinylated rather than polybiotinylated (FIG. 1d, left). A final filtration of coated particles appeared necessary to exclude residual aggregates (FIG. 1d, right). An estimation of the mean number of antigen molecules that can be coated on each nanosphere was obtained by incubating nanospheres with increasing amounts of biotinylated ovalbumin and quantifying ovalbumin binding by flow cytometry with a FITC-conjugated anti-ovalbumin mAb (FIG. 1e). Based on the saturation curve obtained by this method, we evaluated that the number of ovalbumin molecules than can be coated on each SPAg was approaching 10000 (FIG. 1e). The final concentration of SPAg after filtration was measured by spectrophotometry using the standard curve method (FIG. 1f).

Figure 2A:
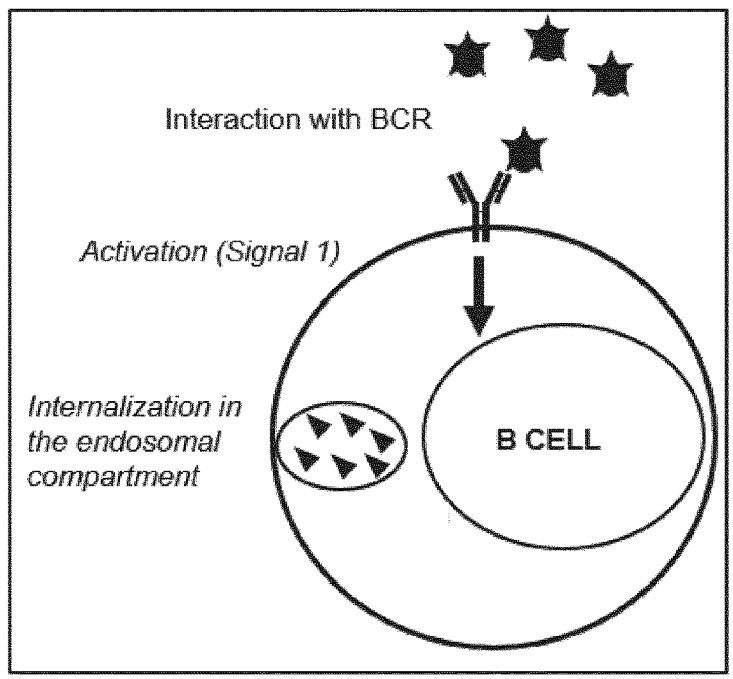
Figure 2B:
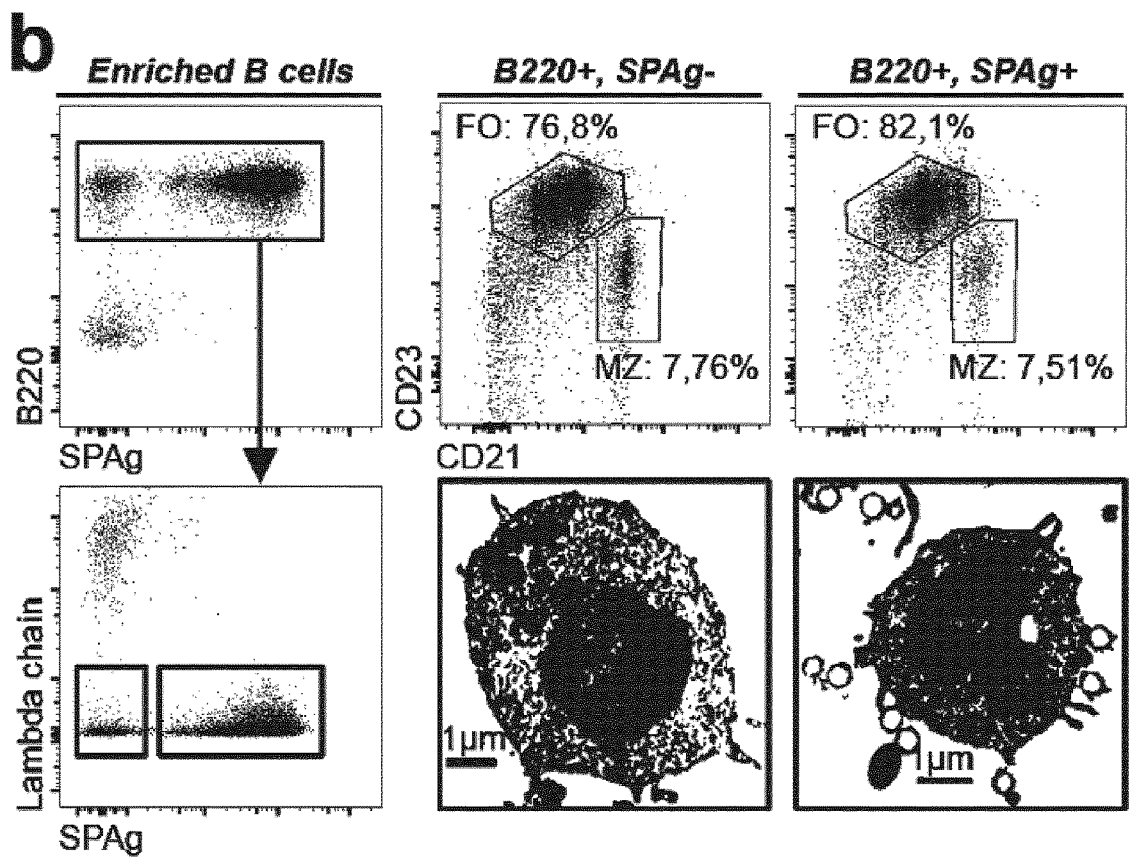
Figure 2C:
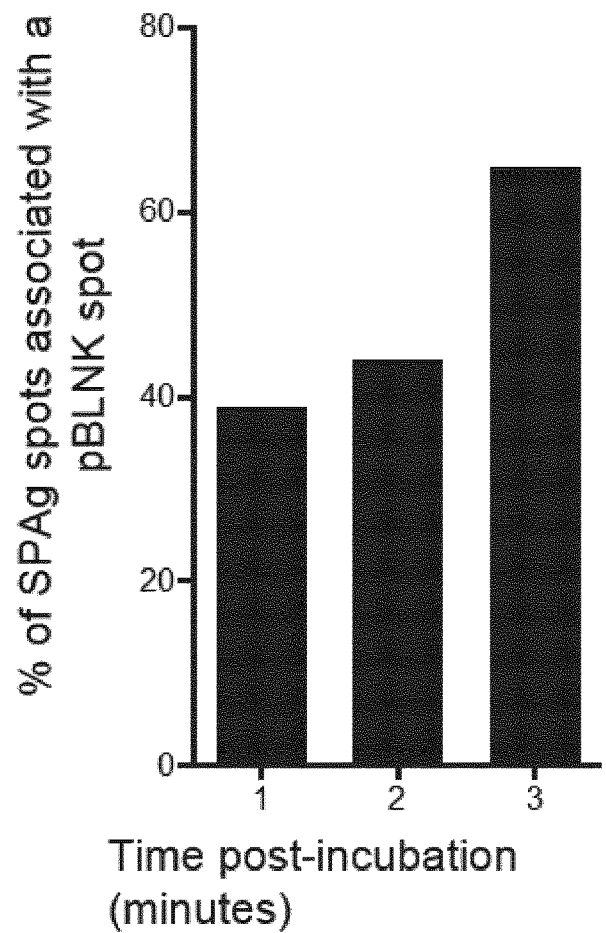
Figure 2D:
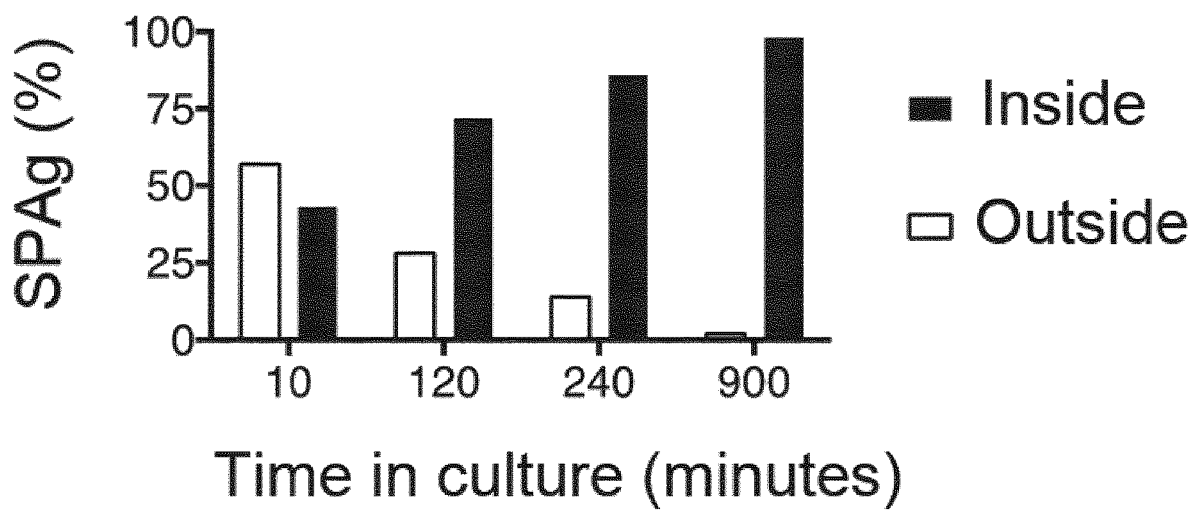
Figure 3A:
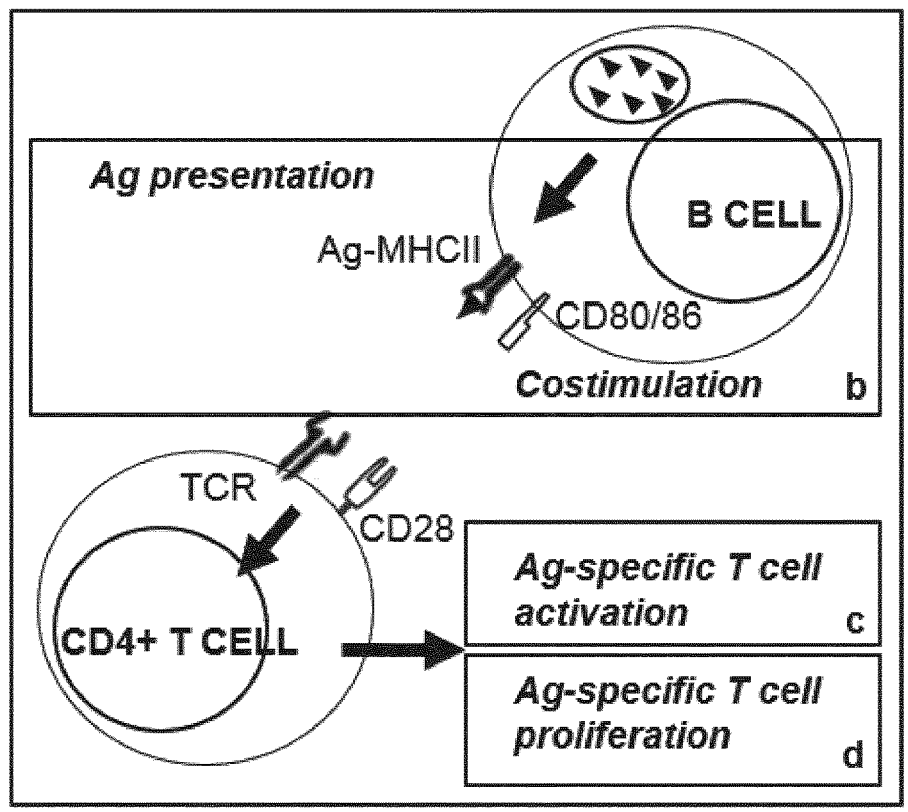
Figure 3B:
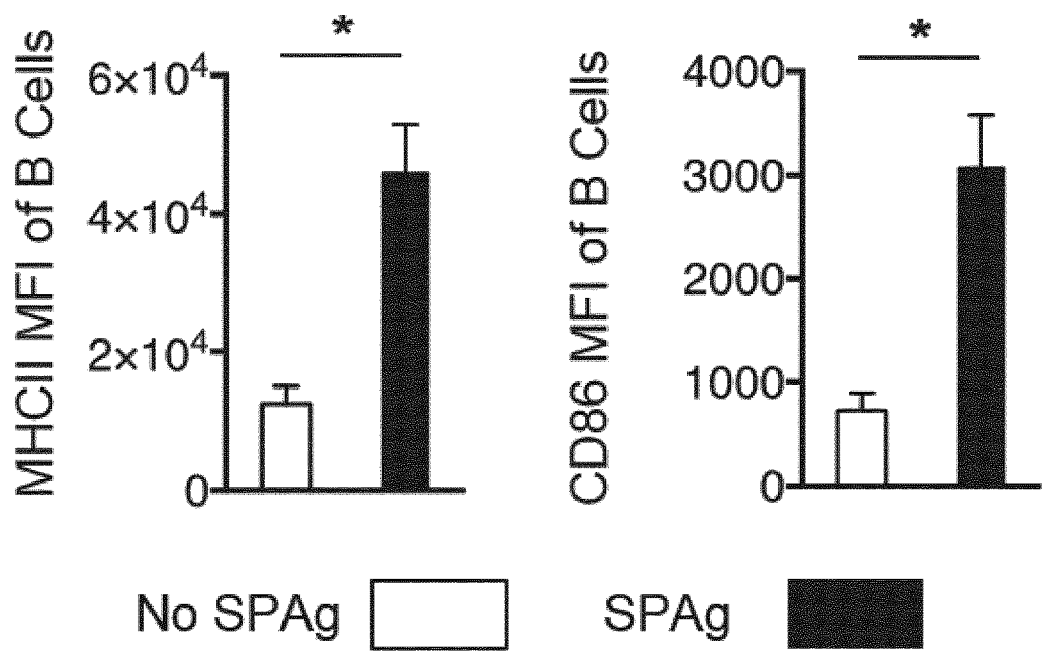
Figure 3C:
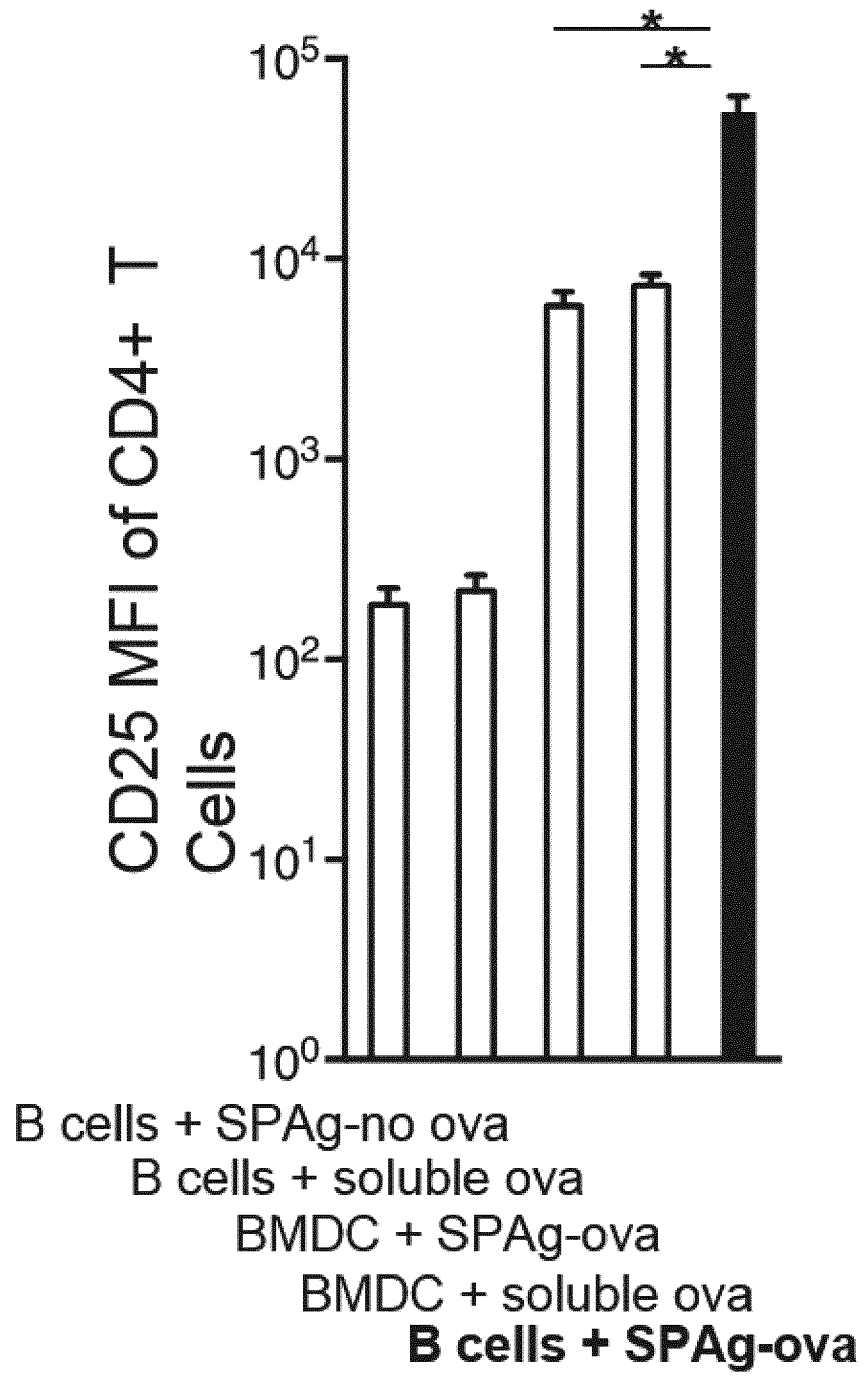
Figure 3D:
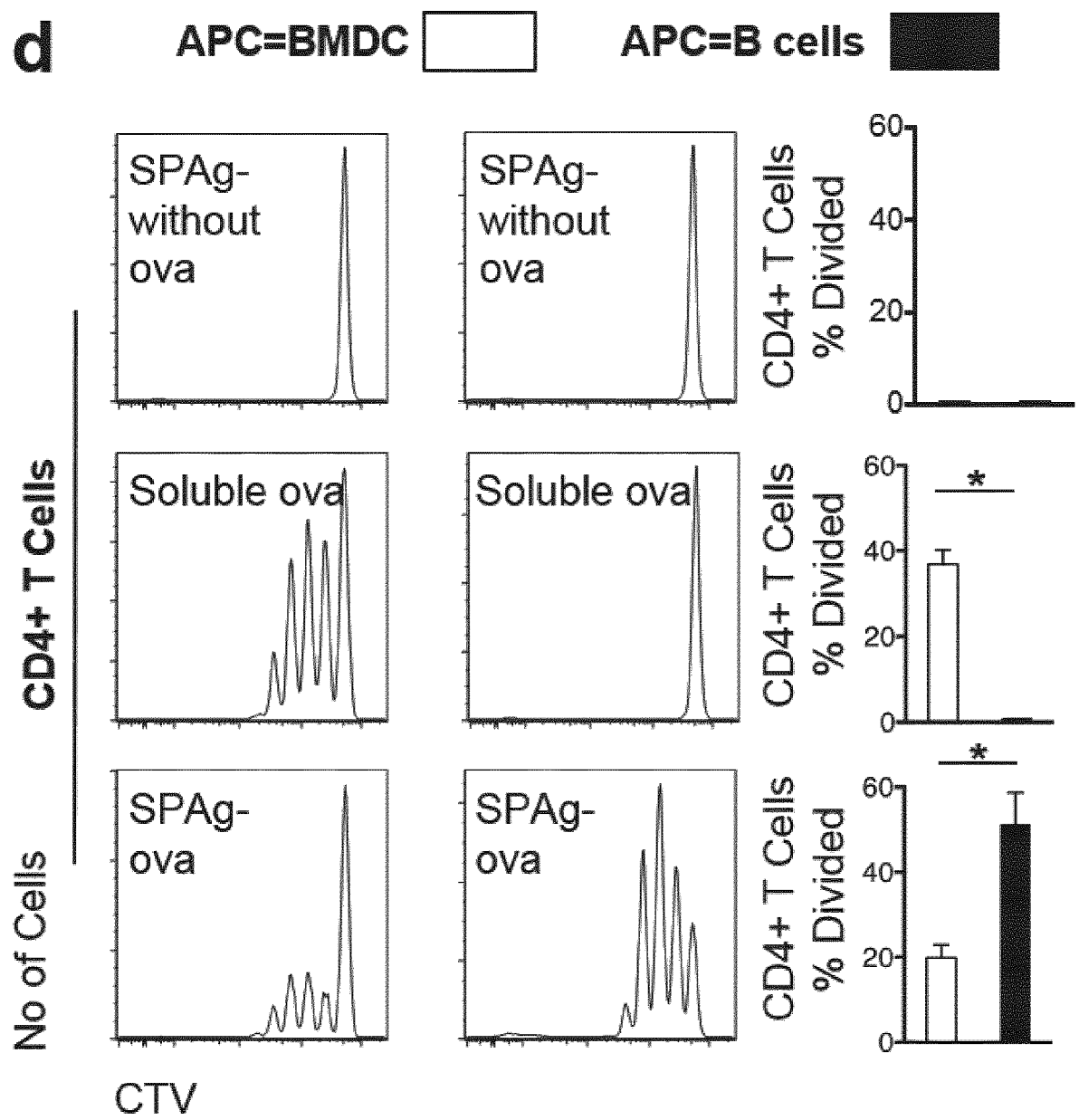

To test the hypothesis that SPAg would bind to any non-cognate kappa positive BCR and behave like genuine antigens, SPAg were incubated in vitro with B cells purified from the spleen of a wild type mice at a 100:1 SPAg to B cell ratio. Each of the steps necessary for antigen-presentation by B cells were analyzed: (i) attachment to surface BCR, (ii) triggering of activation signal and (iii) internalization in late endosomal compartment[37] (FIG. 2a). Flow cytometry analysis showed that SPAg bound exclusively to B220+ lambda chain-B cells, confirming that SPAg interaction with B cells was dependent upon anti-κ mAb (FIG. 2b, left). Noteworthy, SPAg were able to bind with equal efficiency to all B cells with kappa positive BCR, regardless the subset (follicular or marginal zone; FIG. 2b, upper right). Flow cytometry results were confirmed by EM analyses (FIG. 2b, lower right). To assess whether SPAg were able to trigger BCR signaling cascade, as would cognate antigen, imaging flow cytometer was used to detect the phosphorylated form of the B cell linker protein (p-BLNK), an adaptor protein that is phosphorylated upon BCR crosslinking[40] (FIG. 2c). A circular p-BLNK signal was detected in both lambda and kappa positive B lymphocytes, when the cells were activated with anti-IgM soluble Fab'2 (positive control, FIG. 2c upper left). In contrast, incubation of B lymphocytes with SPAg resulted in a punctiform p-BLNK signal, which colocalized with SPAg fluorescence and was only detected in kappa-positive B cells (FIG. 2c lower left). Sixty percent of SPAg bound to B cell surface had triggered BCR signaling at 3 minutes post-incubation (FIG. 2c right). The internalization of SPAg, which is indispensable for antigen presentation, was analyzed by EM (data not shown) and quantified kinetically with imaging flow cytometry (FIG. 2d). After fifteen hours in culture, 98% of SPAg had been internalized in B cells. A confocal microscopy analysis demonstrated the co-localization of SPAg with a marker of late endosomes (Lamp1) and demonstrated that internalized SPAgs were localized in late endosomal compartment, where antigens are processed and loaded onto MHCII (data not shown). In ordinary conditions, the subsequent migration of antigen-MHCII complexes at the surface of B cells and the expression of costimulation molecules (CD80/86) lead to the activation and proliferation of cognate CD4+ clones (FIG. 3a). Consistently, flow cytometry analyses after overnight culture showed a higher expression of MHCII and CD86 in B cells that had internalized SPAg, as compared with B cells that had not been incubated with SPAg (FIG. 3b). The ability of SPAg-loaded B cells (B cells-SPAg-ova) to activate antigen-specific T cells was assessed by measuring the expression of the activation marker CD25 on ova-specific CD4+ T cells from OTII transgenic mice after 72 hours of coculture at a 1:1 B cell to T cell ratio (FIG. 3c). B cells loaded with SPAg without ova (B cells-SPAg-no ova) and B cells pre-incubated with soluble ova (B cells-soluble ova) were used as negative controls whereas bone marrow-derived dendritic cells pulsed with SPAg (BMDC-SPAg) or with soluble ovalbumin (BMDC-soluble ova) were used as positive controls. In contrast with negative controls, B cells-SPAg-ova did activate OTII CD4+ T cells. Importantly, CD25 expression by OTII CD4+ T cells was higher when B cells-SPAg-ova were used as APCs than when BMDC-SPAg or BMDC-soluble ova were used (CD25 MFI=54063±11061 vs 5864±1038 and 7401±1000 respectively, p<0.05, FIG. 3c). SPAg-loaded B cells also induced a higher OTII CD4+ T cells proliferation than BMDC-SPAg-ova or BMDC-soluble ova did (FIG. 3d, % of divided T cells at 72 hours: 51.3±7.4 versus 19.3±3.0 and 36.9±3.3 respectively, p<0.05). As expected, B cells-SPAg-no ova or B cells-soluble ova did not induce CD4+ T cell proliferation (FIG. 3d).

Figure 4A:
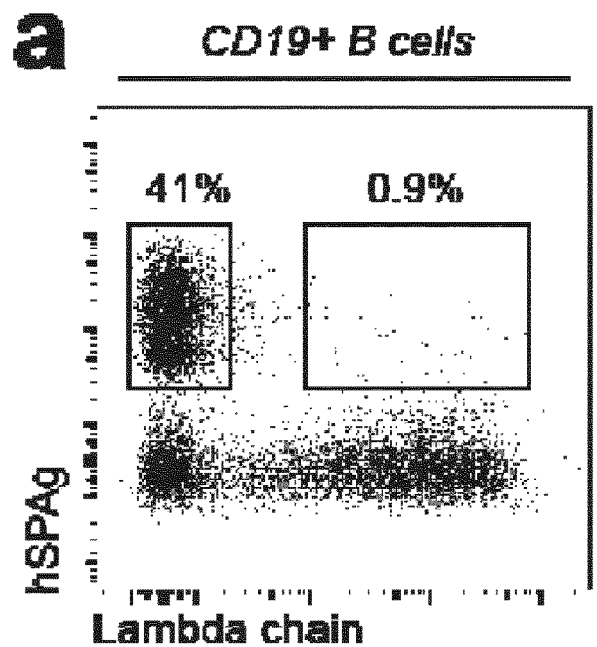
Figure 4B:
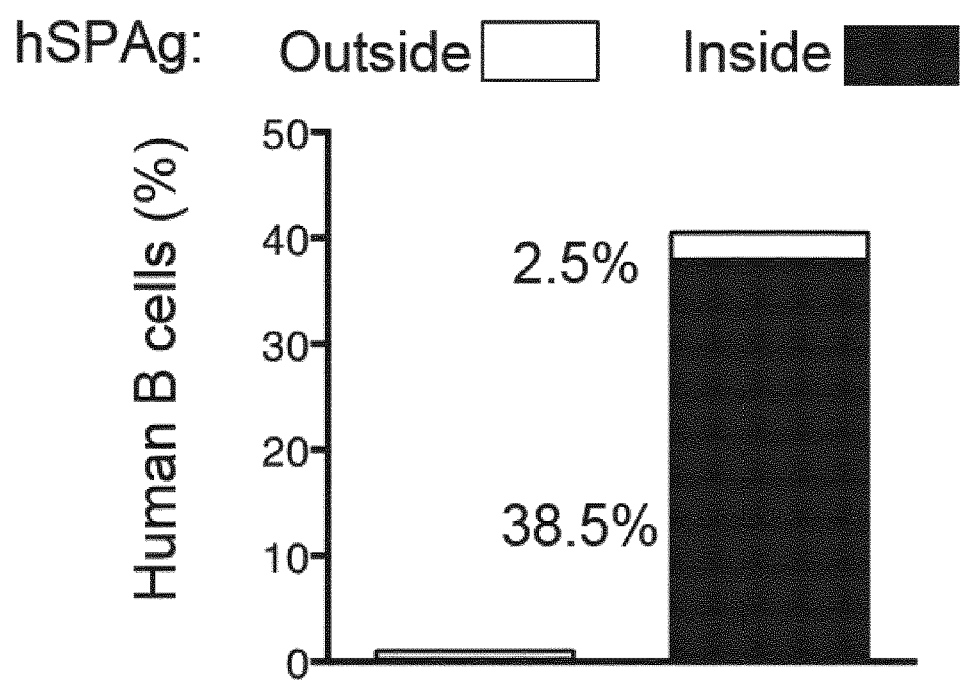

To test the applicability of our approach in humans, B cells purified from the peripheral blood of an healthy volunteer were incubated 30 minutes at 37° C. with SPAg coated with anti-human kappa-light chain mAbs (hSPAg). Flow cytometry analysis revealed that hSPAg bound exclusively to CD19+ lambda chain-B cells, showing that the interaction of hSPAg with B cells is dependent upon anti-κ mAb (FIG. 4a). The internalization of hSPAg by humans B cells was verified by EM (data not shown) and quantified by imaging flow cytometry (FIG. 4b). After 12 hours culture, the proportion of B cells with internalized hSPAg was 38.5%. This relatively low percentage as compared with murine experiments is explained by the fact that the proportion of kappa-positive B cells is lower in humans than in mice (50% versus 90% respectively). Optimizing the efficiency of human B cells loading with hSPAg would simply require to replace anti-human kappa-light chain mAbs with mAbs targeting a framework region present on heavy chains (for example, clone G20-127) or to add anti-lambda mAb (for example, clone 1-155-2) in addition to anti-κ mAb.

Figure 4C:
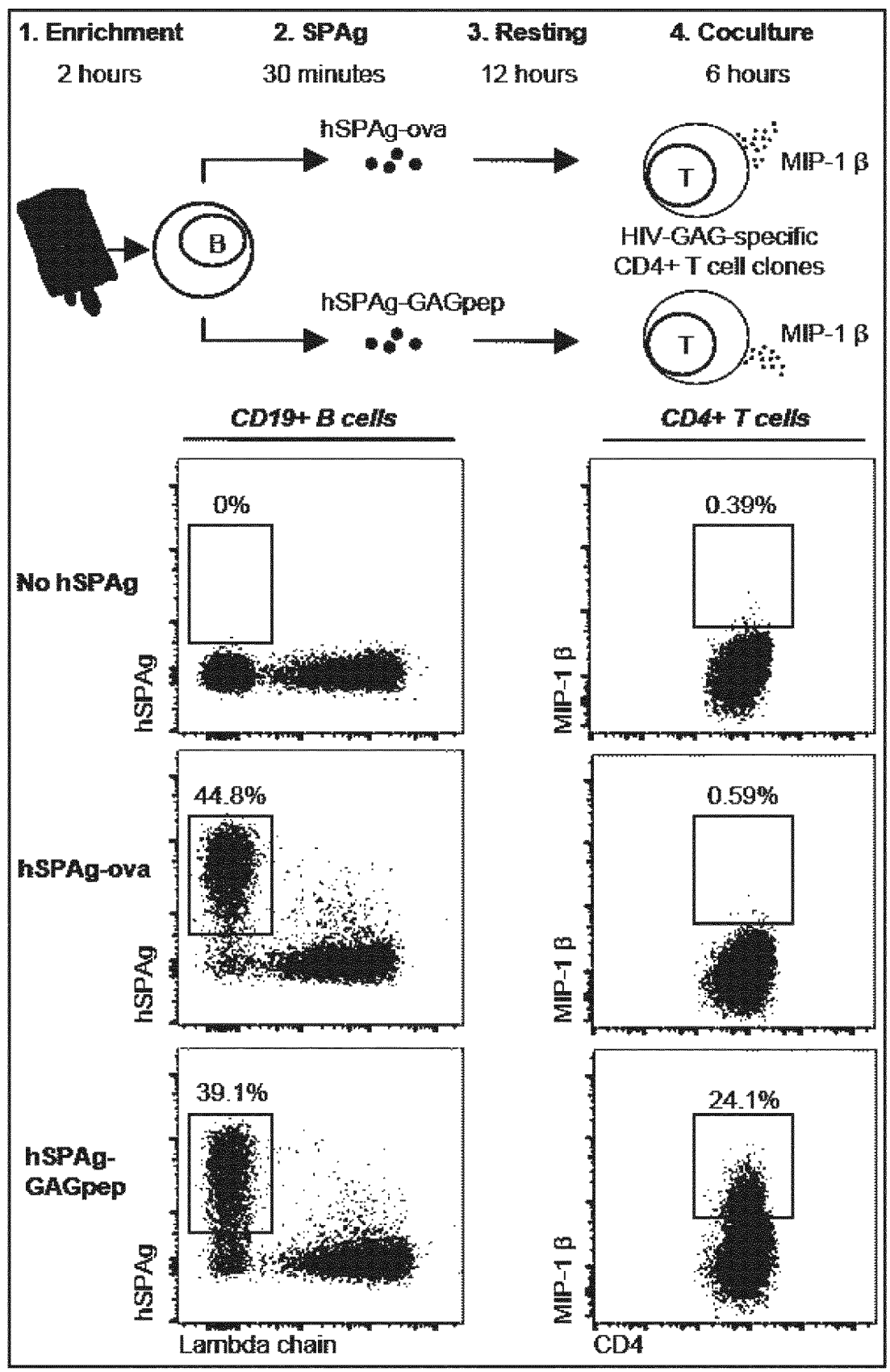

HIV alters CD4+ T cell compartment of patients, hampering the production of broadly neutralizing antibodies[41]. Because educating HIV-specific CD4+ T cells seems particularly relevant in the clinic, we decided to use HIV-GAG protein antigen to test the ability of polyclonal human B cells loaded with hSPAg to present internalized antigen (FIG. 4c). B cells purified from the peripheral blood of a HLA-DR01/01 healthy volunteer were incubated 30 minutes at 37° C. with hSPAg coated with either ovalbumin (use here as negative control, hSPAg-ova) or a peptide made of 3 repetitions of a sequence of HIV-GAG protein (hSPAg-GAG). B cells were then rested 12 hours at 37° C. and coculture 6 hours with HLA-DR01-restricted CD4+ T cell clones specific for the HIV-GAG protein[42]. CD4+ T cell clones activation was assessed by flow-cytometry measurement of the intracellular cytokine MIP-1β. The percentage of B cells loaded with hSPAg-ova and hSPAg-GAG were comparable (44.8% and 39.1% respectively). As expected, unloaded B cells and B cells loaded with hSPAg-ova did not induce production of MIP-1β by CD4+ T cell clones (0.39% and 0.59% of positive clones respectively). In contrast, 24.1% of clones did produce MIP-1β when cocultured with B cells loaded with hSPAg-GAG. This result demonstrates that SPAg can be used to induce efficient antigen presentation by human polyclonal B cells to cognate CD4+ T cells.

Figure 5A:
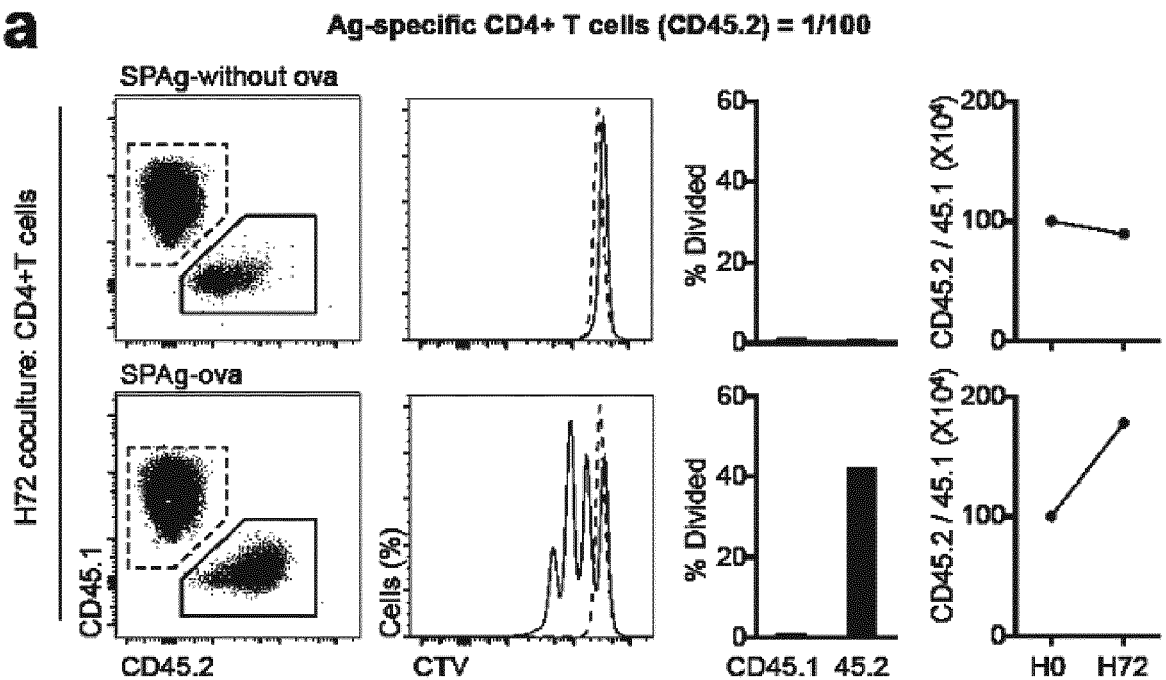
Figure 5B:
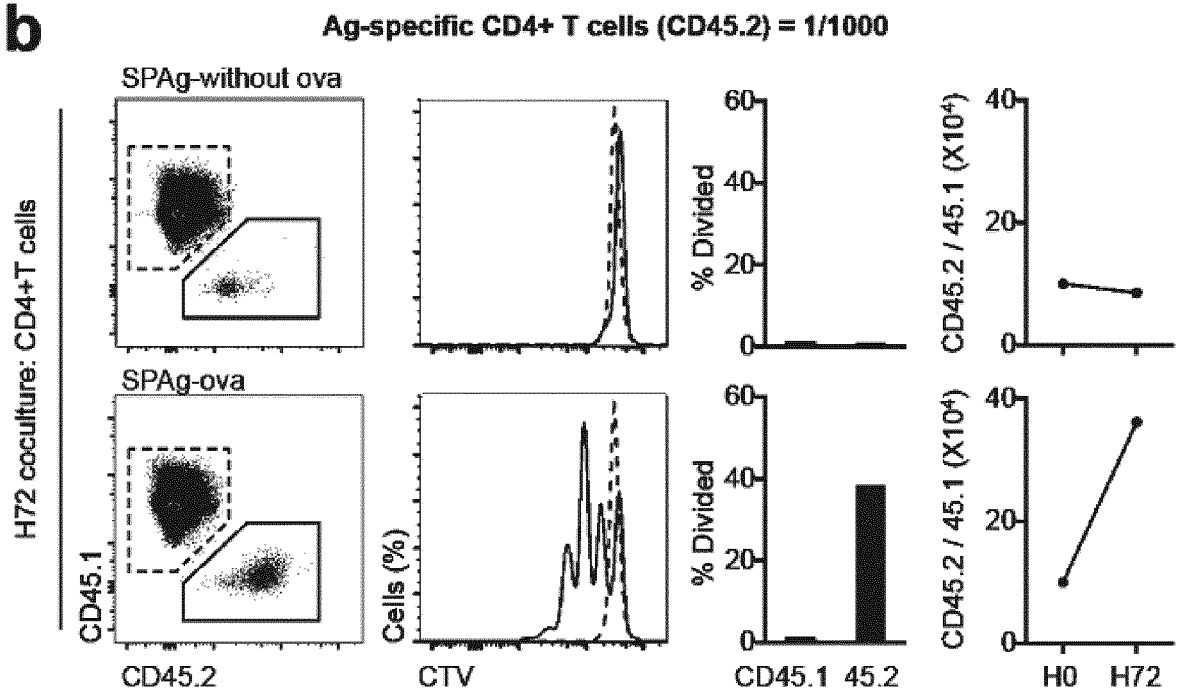
Figure 5C:
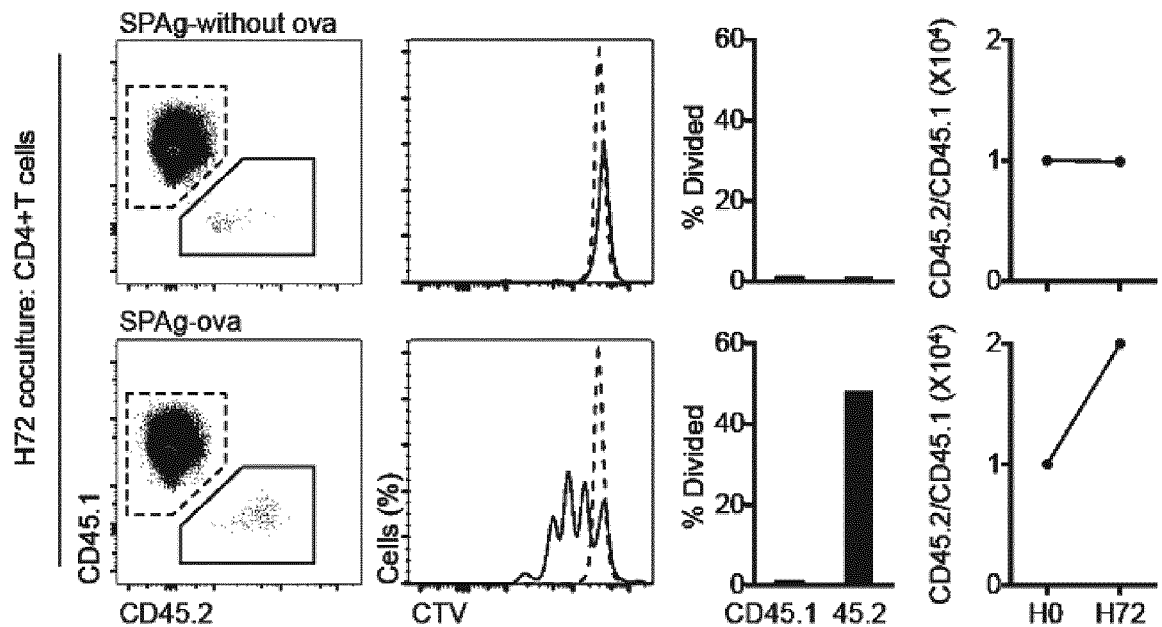

Because CD4+ T cells specific for a given epitope are rare in the general CD4+ T cell population (as low as 1/100 in the memory compartment and below 1/10000 in the naïve repertoire[20]), the capacity of SPAg-loaded B cells to expand rare antigen-specific T cells populations was tested in our murine experimental setting (FIG. 5). B cells-SPAg-no ova and B cells-SPAg-ova were cultured 72 hours with a mix of cognate OTII CD4+ T cells (CD45.2) and polyclonal CD4+ T cells (CD45.1). Various cognate to polyclonal T cells ratios were tested: 1/100 (FIG. 5a), 1/1000 (FIG. 5b) or 1/10000 (FIG. 5c). At any ratios, B cells-SPAg-ova, but not B cells-SPAg-no ova, induced specific proliferation of cognate T cells. CD45.2/CD45.1 ratios increased more than two times during the 72 hours of cocultures. Thus, SPAg-loaded B cells can induce proliferation and expansion of rare cognate CD4+ T cells.

As discussed above, CD4+ T cells exert different roles according to the pathophysiological context. Upon TCR-mediated activation, the nature of the microenvironment guide them towards particular functions, a processed called polarization (for recent review see:[16]). There is compelling evidences in the literature that Th1 polarized effector CD4+ T cells, which produce high levels of the proinflammatory cytokine IFNγ, are more efficient in promoting immune responses against virus and cancers[10,43,44]. In contrast, regulatory CD4+ T cells (CD4+ Treg), which are characterized by the expression of the transcription factor Forkhead box P3 (Foxp3)[45], are specialized in promoting the tolerance towards the auto- and allo-antigens for which they are specific[46,47]. Be able to polarize antigen-specific CD4+ T cell toward the adequate profile is therefore essential for the success of ACT. To test whether it is possible to polarize antigen-specific CD4+ T cells upon activation with SPAg-loaded B cells, a presentation assay was performed under polarizing conditions (FIG. 6a). SPAg-loaded B cells were cocultured 5 days with OTII CD4+ T cells in media without exogenous cytokines (Th0), with recombinant IL12 (Th1 polarizing media) or with TGFPβ (Treg polarizing media). Flow cytometry analyses showed that CD4+ T cells produced IFNγ only under Th1 polarizing conditions and expressed Foxp3 only under Treg polarizing conditions. Even if adequate polarization could be obtained by adding exogenous cytokine to the culture media, it is likely that this method does not entirely reproduce the complexity of the polarization process that takes place in vivo that depends not only on the nature of cytokines present in the microenvironment but also on the type of costimulation signals delivered by APCs[16]. B cells have been shown, both in animal models[48] and in humans[49], to be endowed with unique regulatory functions[50,51]. Regulatory B cells (Breg) inhibit effector CD4+ T cell (Teff) responses and promotes Treg differentiation through the production of suppressive cytokines (in particular IL10) and cell-to-cell crosstalk[48,50,52] Importantly, it has been shown that B cells stimulated in vitro with high doses of toll like receptors (TLR) ligands acquire regulatory properties[53,54]. Based on these observations, we assumed that regulatory properties could be conferred to SPAg-loaded B cells by adding CpG (the ligand of TLR9) to the culture (FIG. 6b). We hypothesized that Bregs loaded with SPAg (Breg-SPAg) would generate antigen-specific Tregs ex vivo without the need for addition of exogenous cytokines (FIG. 6b). Beyond its simplicity and reduced cost, this approach would also harness all the physiological mechanisms used by Breg to inhibit Teff and induce Treg. To define whether SPAg-loaded B cells secrete IL10 upon CpG stimulation, B cells-SPAg from IL10-reporter mice (IL10-IRES-eGFP transgenic mice[55]) were cultured 48 hours in medium supplemented with either anti-CD40 agonist (negative control, B cells-SPAg-40) or CpG (B reg-SPAg) (FIG. 6c). The proportion of SPAg-positive B cells expressing eGFP was measured by flow cytometry kinetically. In contrast with anti-CD40 stimulation, CpG stimulation resulted in IL10 production by B cells-SPAg (FIG. 6c, black and green curves respectively). The number of eGFP+ SPAg+ B cells peaked at 36 hours of culture (24.6%). We next went on analyzing whether Breg-SPAg could be used to promote the expansion of antigen-specific Treg. OTII CD4+ T cells were cultured with sorted B cells-SPAg that had been prestimulated 36 hours with either anti-CD40 agonist (Beff-SPAg) or CpG (Breg-SPAg) (FIG. 6d). B cells without SPAg prestimulated with anti-CD40 or CpG (Beff-noSPAg and B reg-noSPAg respectively) were used as negative controls. The proportion and proliferation profiles of Treg (CD4+ Foxp3+) and Teff (CD4+ Foxp3-) were kinetically assessed by flow cytometry over 5 days culture (FIG. 6d). In line with our hypothesis, a progressive increase in the proportion of Treg was observed only when OTII CD4+ T cells were cocultured with Breg-SPAg (FIG. 6d, left). This was due to the fact that Breg-SPAg did not induce a significant proliferation of Teff but promoted instead the proliferation of antigen-specific Treg (FIG. 6d right). Contrariwise, Beff-SPAg induced the proliferation of Teff but not of Treg.

In this study, we present a novel versatile approach to expand and polarize antigen-specific CD4+ T cells that could be used in ACT. Our work indeed demonstrates that nanospheres can be easily biofunctionalized to behave like synthetic particulate antigen (SPAg) able to simultaneously i) activate polyclonal B lymphocytes, and ii) deliver any antigen of interest into the endosomal compartment of these B lymphocytes, thus turning non-cognate B cells into highly efficient stimulators of antigen-specific CD4+ T cells. Furthermore, this technique offers the possibility to harness the unique ability of B cells to polarize CD4+ T cells into either effectors or regulators.

In contrast with DCs, which currently represent the gold standard for ex vivo stimulation of antigen-specific CD4+ T cells, B cells are readily accessible in peripheral blood and can be conveniently and cheaply expanded by logs in vitro, offering an almost inexhaustible fresh source of highly pure autologous APCs[31,32]. These decisive advantages had led several groups to explore the possibility of exploiting the antigen presentation function of B cells for purpose of cell therapy[31-33,56-67]. In organ transplantation, donor's B cells have been shown to be more efficient than donor's DC to expand ex vivo graft-specific Tregs[68]. Since donor's HLA (which is the molecular target in rejection) is expressed on the surface of donor's B lymphocytes, these cells can be directly used to expand graft-specific CD4+ Treg[56,57]. However, in all other pathophysiological situations, B cells must first be loaded with the chosen exogenous antigen before being able to interact with CD4+ T cells. This point is challenging because cognate interactions of antigen with the BCR are required for effective internalization, processing and presentation of the antigen by B cells[36-38]. Several strategies have been tested to overcome this limitation. The group of Dr. Scott pioneered this field and showed that cloning the target protein in frame with an immunoglobulin heavy chain and delivering it via retrovirus to an activated B cell could be a strategy to induce tolerance to multiple epitopes[58-60]. This strategy has however some drawbacks that limit its translation in the clinic. The generation of vectors can be technically challenging, the size of the inserts coding for the antigenic sequences is limited, and long-term gene transfer into primary human B cells is known to be notoriously difficult[69-71]. Finally, this approach lack versatility since the whole process needs to be set up again each time the antigen is changed. More recently, Lee Szeto et al have used a microfluidic device to deliver antigens in solution to polyclonal B cells via mechano-poration[63]. With this method, whole proteins cross the plasma membrane through transient pores without any selective uptake by BCR. As a result, the antigen, which is not vectorized in the endosomal compartment of B cells, can only be loaded into the MHCI, limiting the technique to the generation of antigen-specific cytotoxic CD8+ T cells. SPAg offer several advantages: i) the antigen is delivered to polyclonal B cells through the BCR, i.e. the physiological route of antigen uptake, ii) antigens can be delivered to B cells in their native form without any important engineering, and iii) SPAg-loaded B cells process the whole antigen, ensuring a natural and exhaustive generation of distinct antigenic peptides. As a result, SPAg-based technology is cheap, fast (<1 hour) and accessible to all biologists (no need for specialized skills or equipments) while remaining highly efficient to promote the presentation of any antigen in the MHCII of polyclonal B cells.

Finally, although the present work only details the use of SPAg to generate antigen-specific CD4+ T cell ex vivo, the possibility to directly use SPAg-loaded B cells in vivo to treat patients shouldn't be ignored. B cells have indeed the ability to home to patient's secondary lymphoid organs[72]. There, SPAg-loaded B cells could act as a cellular vaccine to promote the development of an endogenous response against cancers or persistent virus infections. Alternatively, the transfer of SPAg-loaded regulatory B cells could promote tolerance in transplant recipients or patients with autoimmune diseases. Further studies in animal models are warranted to assess the therapeutic potentials and risks of such strategies.

REFERENCES

1. Eberlein T J, Rosenstein M, Rosenberg S A: Regression of a disseminated syngeneic solid tumor by systemic transfer of lymphoid cells expanded in interleukin 2. *J. Exp. Med.* 156: 385-397, 1982
2. Rosenberg S A, Restifo N P: Adoptive cell transfer as personalized immunotherapy for human cancer. *Science* 348: 62-68, 2015
3. Rosenberg S A, Packard B S, Aebersold P M, Solomon D, Topalian S L, Toy S T, Simon P, Lotze M T, Yang J C, Seipp C A: Use of tumor-infiltrating lymphocytes and interleukin-2 in the immunotherapy of patients with metastatic melanoma. A preliminary report. *N. Engl. J. Med.* 319: 1676-1680, 1988
4. Walter E A, Greenberg P D, Gilbert M J, Finch R J, Watanabe K S, Thomas E D, Riddell S R: Reconstitution of cellular immunity against cytomegalovirus in recipients of allogeneic bone marrow by transfer of T-cell clones from the donor. *N. Engl. J. Med.* 333: 1038-1044, 1995
5. Brodie S J, Lewinsohn D A, Patterson B K, Jiyamapa D, Krieger J, Corey L, Greenberg P D, Riddell S R: In vivo migration and function of transferred HIV-1-specific cytotoxic T cells. *Nat Med* 5: 34-41, 1999
6. Mackensen A, Meidenbauer N, Vogl S, Laumer M, Berger J, Andreesen R: Phase I study of adoptive T-cell therapy using antigen-specific CD8+ T cells for the treatment of patients with metastatic melanoma. *J. Clin. Oncol.* 24: 5060-5069, 2006
7. Yee C, Thompson J A, Byrd D, Riddell S R, Roche P, Celis E, Greenberg P D: Adoptive T cell therapy using antigen-specific CD8+ T cell clones for the treatment of patients with metastatic melanoma: in vivo persistence, migration, and antitumor effect of transferred T cells. *Proc. Natl. Acad. Sci. U.S.A.* 99: 16168-16173, 2002
8. Muranski P, Restifo N P: Adoptive immunotherapy of cancer using CD4(+) T cells. *Current Opinion in Immunology* 21: 200-208, 2009
9. Kamphorst A O, Ahmed R: CD4 T-cell immunotherapy for chronic viral infections and cancer. *Immunotherapy* 5: 975-987, 2013
10. Swain S L, McKinstry K K, Strutt T M: Expanding roles for CD4+ T cells in immunity to viruses. *Nat. Rev. Immunol.* 12: 136-148, 2012
11. Kennedy R, Celis E: Multiple roles for CD4+ T cells in anti-tumor immune responses. *Immunol. Rev.* 222: 129-144, 2008
12. Heller K N, Gurer C, Münz C: Virus-specific CD4+ T cells: ready for direct attack. *J. Exp. Med.* 203: 805-808, 2006
13. Nakanishi Y, Lu B, Gerard C, Iwasaki A: CD8+ T lymphocyte mobilization to virus-infected tissue requires CD4+ T-cell help. *Nature* 462: 510-513, 2009
14. Sun J C: Defective CD8 T Cell Memory Following Acute Infection Without CD4 T Cell Help. *Science* 300: 339-342, 2003
15. Tangye S G, Ma C S, Brink R, Deenick E K: The good, the bad and the ugly-TFH cells in human health and disease. *Nat. Rev. Immunol.* 13: 412-426, 2013
16. Geginat J, Paroni M, Maglie S, Alfen J S, Kastirr I, Gruarin P, De Simone M, Pagani M, Abrignani S: Plasticity of human CD4 T cell subsets. *Front Immunol* 5: 630, 2014
17. Sagoo P, Ali N, Garg G, Nestle F O, Lechler R I, Lombardi G: Human regulatory T cells with alloantigen specificity are more potent inhibitors of alloimmune skin graft damage than polyclonal regulatory T cells. *Sci Transl Med* 3: 83ra42-83ra42, 2011
18. Hunder N N, Wallen H, Cao J, Hendricks D W, Reilly J Z, Rodmyre R, Jungbluth A, Gnjatic S, Thompson J A, Yee C: Treatment of metastatic melanoma with autologous CD4+ T cells against NY-ESO-1. *N. Engl. J. Med.* 358: 2698-2703, 2008
19. Tran E, Turcotte S, Gros A, Robbins P F, Lu Y-C, Dudley M E, Wunderlich J R, Somerville R P, Hogan K, Hinrichs C S, Parkhurst M R, Yang J C, Rosenberg S A: Cancer immunotherapy based on mutation-specific CD4+ T cells in a patient with epithelial cancer. *Science* 344: 641-645, 2014
20. Geiger R, Duhen T, Lanzavecchia A, Sallusto F: Human naive and memory CD4+ T cell repertoires specific for naturally processed antigens analyzed using libraries of amplified T cells. *J. Exp. Med.* 206: 1525-1534, 2009
21. Kim J V, Latouche J-B, Rivière I, Sadelain M: The ABCs of artificial antigen presentation. *Nat. Biotechnol.* 22: 403-410, 2004
22. Perica K, Tu A, Richter A, Bieler J G, Edidin M, Schneck J P: Magnetic field-induced T cell receptor clustering by nanoparticles enhances T cell activation and stimulates antitumor activity. *ACS Nano* 8: 2252-2260, 2014
23. Molino N M, Anderson A K L, Nelson E L, Wang S-W: Biomimetic protein nanoparticles facilitate enhanced dendritic cell activation and cross-presentation. *ACS Nano* 7: 9743-9752, 2013

24. Fadel T R, Steenblock E R, Stern E, Li N, Wang X, Haller G L, Pfefferle L D, Fahmy T M: Enhanced cellular activation with single walled carbon nanotube bundles presenting antibody stimuli. *Nano Lett.* 8: 2070-2076, 2008

25. Matic J, Deeg J, Scheffold A, Goldstein I, Spatz J P: Fine Tuning and Efficient T Cell Activation with Stimulatory aCD3 Nanoarrays. *Nano Lett.* 13: 5090-5097, 2013

26. Delcassian D, Depoil D, Rudnicka D, Liu M, Davis D M, Dustin M L, Dunlop I E: Nanoscale ligand spacing influences receptor triggering in T cells and NK cells. *Nano Lett.* 13: 5608-5614, 2013

27. Fadel T R, Sharp F A, Vudattu N, Ragheb R, Garyu J, Kim D, Hong E, Li N, Haller G L, Pfefferle L D, Justesen S, Herold K C, Harold K C, Fahmy T M: A carbon nanotube-polymer composite for T-cell therapy. *Nat Nanotechnol* 9: 639-647, 2014

28. Ataman-Onal Y, Munier S, Ganée A, Terrat C, Durand P-Y, Battail N, Martinon F, Le Grand R, Charles M-H, Delair T, Verrier B: Surfactant-free anionic PLA nanoparticles coated with HIV-1 p24 protein induced enhanced cellular and humoral immune responses in various animal models. *J Control Release* 112: 175-185, 2006

29. Eggermont L J, Paulis L E, Tel J, Figdor C G: Towards efficient cancer immunotherapy: advances in developing artificial antigen-presenting cells. *Trends Biotechnol.* 32: 456-465, 2014

30. Schlienger K, Craighead N, Lee K P, Levine B L, June C H: Efficient priming of protein antigen-specific human CD4(+) T cells by monocyte-derived dendritic cells. *Blood* 96: 3490-3498, 2000

31. Wennhold K, Shimabukuro-Vornhagen A, Theurich S, Bergwelt-Baildon von M: CD40-activated B cells as antigen-presenting cells: the final sprint toward clinical application. *Expert Rev Vaccines* 12: 631-637, 2013

32. Kondo E, Gryschok L, Klein-Gonzalez N, Rademacher S, Weihrauch M R, Liebig T, Shimabukuro-Vornhagen A, Kochanek M, Draube A, Bergwelt-Baildon von MS: CD40-activated B cells can be generated in high number and purity in cancer patients: analysis of immunogenicity and homing potential. *Clinical & Experimental Immunology* 155: 249-256, 2009

33. Schultze J L, Michalak S, Seamon M J, Dranoff G, Jung K, Daley J, Delgado J C, Gribben J G, Nadler L M: CD40-activated human B cells: an alternative source of highly efficient antigen presenting cells to generate autologous antigen-specific T cells for adoptive immunotherapy. *J. Clin. Invest.* 100: 2757-2765, 1997

34. Cavanagh L L, Saal R J, Grimmett K L, Thomas R: Proliferation in monocyte-derived dendritic cell cultures is caused by progenitor cells capable of myeloid differentiation. *Blood* 92: 1598-1607, 1998

35. Trombetta E S, Mellman I: CELL BIOLOGY OF ANTIGEN PROCESSING IN VITRO AND IN VIVO. *Annu. Rev. Immunol.* 23: 975-1028, 2005

36. Harwood N E, Batista F D: Early Events in B Cell Activation. *Annu. Rev. Immunol.* 28: 185-210, 2010

37. Avalos A M, Ploegh H L: Early BCR Events and Antigen Capture, Processing, and Loading on MHC Class II on B Cells. *Front Immunol* 5: 92, 2014

38. Depoil D, Weber M, Treanor B, Fleire S J, Carrasco Y R, Harwood N E, Batista F D: Early events of B cell activation by antigen. *Sci Signal* 2: pt1-pt1, 2009

39. Thaunat O, Granja A G, Barral P, Filby A, Montaner B, Collinson L, Martinez-Martin N, Harwood N E, Bruckbauer A, Batista F D: Asymmetric segregation of polarized antigen on B cell division shapes presentation capacity. *Science* 335: 475-479, 2012

40. Wienands J, Schweikert J, Wollscheid B, Jumaa H, Nielsen P J, Reth M: SLP-65: a new signaling component in B lymphocytes which requires expression of the antigen receptor for phosphorylation. *J. Exp. Med.* 188: 791-795, 1998

41. Yamamoto T, Lynch R M, Gautam R, Matus-Nicodemos R, Schmidt S D, Boswell K L, Darko S, Wong P, Sheng Z, Petrovas C, McDermott A B, Seder R A, Keele B F, Shapiro L, Douek D C, Nishimura Y, Mascola J R, Martin M A, Koup R A: Quality and quantity of TFH cells are critical for broad antibody development in SHIVAD8 infection. *Sci Transl Med* 7: 298ra120-298ra120, 2015

42. Moris A, Pajot A, Blanchet F, Guivel-Benhassine F, Salcedo M, Schwartz O: Dendritic cells and HIV-specific CD4+ T cells: HIV antigen presentation, T-cell activation, and viral transfer. *Blood* 108: 1643-1651, 2006

43. Maloy K J, Burkhart C, Junt T M, Odermatt B, Oxenius A, Piali L, Zinkernagel R M, Hengartner H: CD4(+) T cell subsets during virus infection. Protective capacity depends on effector cytokine secretion and on migratory capability. *J. Exp. Med.* 191: 2159-2170, 2000

44. Dunn G P, Koebel C M, Schreiber R D: Interferons, immunity and cancer immunoediting. *Nat. Rev. Immunol.* 6: 836-848, 2006

45. Fontenot J D, Gavin M A, Rudensky A Y: Foxp3 programs the development and function of CD4+CD25+ regulatory T cells. *Nat. Immunol.* 4: 330-336, 2003

46. Brusko T M, Putnam A L, Bluestone J A: Human regulatory T cells: role in autoimmune disease and therapeutic opportunities. *Immunol. Rev.* 223: 371-390, 2008

47. Ferrer I R, Hester J, Bushell A, Wood K J: Induction of transplantation tolerance through regulatory cells: from mice to men. *Immunol. Rev.* 258: 102-116, 2014

48. Fillatreau S, Sweenie C H, McGeachy M J, Gray D, Anderton S M: B cells regulate autoimmunity by provision of IL-10. *Nat. Immunol.* 3: 944-950, 2002

49. Blair P A, Norefia L Y, Flores-Borja F, Rawlings D J, Isenberg D A, Ehrenstein M R, Mauri C: CD19(+)CD24(hi)CD38(hi) B cells exhibit regulatory capacity in healthy individuals but are functionally impaired in systemic Lupus Erythematosus patients. *Immunity* 32: 129-140, 2010

50. Mauri C, Bosma A: Immune regulatory function of B cells. *Annu. Rev. Immunol.* 30: 221-241, 2012

51. Thaunat O, Morelon E, Defrance T: Am"B" valent: anti-CD20 antibodies unravel the dual role of B cells in immunopathogenesis. *Blood* 116: 515-521, 2010

52. Chesneau M, Michel L, Dugast E, Chenouard A, Baron D, Pallier A, Durand J, Braza F, Guerif P, Laplaud D-A, Soulillou J-P, Giral M, Degauque N, Chiffoleau E, Brouard S: Tolerant Kidney Transplant Patients Produce B Cells with Regulatory Properties. *J. Am. Soc. Nephrol.* 2015

53. Lampropoulou V, Calderon-Gomez E, Roch T, Neves P, Shen P, Stervbo U, Boudinot P, Anderton S M, Fillatreau S: Suppressive functions of activated B cells in autoimmune diseases reveal the dual roles of Toll-like receptors in immunity. *Immunol. Rev.* 233: 146-161, 2010

54. Lampropoulou V, Hoehlig K, Roch T, Neves P, Gomez E C, Sweenie C H, Hao Y, Freitas A A, Steinhoff U, Anderton S M, Fillatreau S: TLR-Activated B Cells Suppress T Cell-Mediated Autoimmunity. *J. Immunol.* 180: 4763-4773, 2008

55. Madan R, Demircik F, Surianarayanan S, Allen J L, Divanovic S, Trompette A, Yogev N, Gu Y, Khodoun M, Hildeman D, Boespflug N, Fogolin M B, Gröbe L, Greweling M, Finkelman F D, Cardin R, Mohrs M, Muller W, Waisman A, Roers A, Karp C L: Nonredundant roles for B cell-derived IL-10 in immune counter-regulation. *J. Immunol.* 183: 2312-2320, 2009

56. Landwehr-Kenzel S, Issa F, Luu S H, Schmück M, Lei H, Zobel A, Thiel A, Babel N, Wood K, Volk H D, Reinke P: Novel GMP-Compatible Protocol Employing an Allogeneic B Cell Bank for Clonal Expansion of Allospecific Natural Regulatory T Cells. *Am J Transplant* 14: 594-606, 2014

57. Tu W, Lau Y-L, Zheng J, Liu Y, Chan P-L, Mao H, Dionis K, Schneider P, Lewis D B: Efficient generation of human alloantigen-specific CD4+ regulatory T cells from naive precursors by CD40-activated B cells. *Blood* 112: 2554-2562, 2008

58. Kang Y, Melo M, Deng E, Tisch R, El-Amine M, Scott D W: Induction of hyporesponsiveness to intact foreign protein via retroviral-mediated gene expression: the IgG scaffold is important for induction and maintenance of immune hyporesponsiveness. *Proc. Natl. Acad. Sci. U.S.A.* 96: 8609-8614, 1999

59. Agarwal R K, Kang Y, Zambidis E, Scott D W, Chan C C, Caspi R R: Retroviral gene therapy with an immunoglobulin-antigen fusion construct protects from experimental autoimmune uveitis. *J. Clin. Invest.* 106: 245-252, 2000

60. Skupsky J, Zhang A-H, Su Y, Scott D W: B-cell-delivered gene therapy induces functional T regulatory cells and leads to a loss of antigen-specific effector cells. *Mol. Ther.* 18: 1527-1535, 2010

61. Calderon-Gomez E, Lampropoulou V, Shen P, Neves P, Roch T, Stervbo U, Rutz S, Kühl AA, Heppner F L, Loddenkemper C, Anderton S M, Kanellopoulos J M, Charneau P, Fillatreau S: Reprogrammed quiescent B cells provide an effective cellular therapy against chronic experimental autoimmune encephalomyelitis. *Eur. J. Immunol.* 41: 1696-1708, 2011

62. Mason N J, Coughlin C M, Overley B, Cohen J N, Mitchell E L, Colligon T A, Clifford C A, Zurbriggen A, Sorenmo K U, Vonderheide R H: RNA-loaded CD40-activated B cells stimulate antigen-specific T-cell responses in dogs with spontaneous lymphoma. *Gene Ther.* 15: 955-965, 2008

63. Lee Szeto G, Van Egeren D, Worku H, Sharei A, Alejandro B, Park C, Frew K, Brefo M, Mao S, Heimann M, Langer R, Jensen K, Irvine D J: Microfluidic squeezing for intracellular antigen loading in polyclonal B-cells as cellular vaccines. *Nature Publishing Group* 5: 10276, 2015

64. Zentz C, Wiesner M, Man S, Frankenberger B, Wollenberg B, Hillemanns P, Zeidler R, Hammerschmidt W, Moosmann A: Activated B cells mediate efficient expansion of rare antigen-specific T cells. *Hum. Immunol.* 68: 75-85, 2007

65. Fujiwara H, Melenhorst J J, Ouriaghli El F, Kajigaya S, Grube M, Sconocchia G, Rezvani K, Price D A, Hensel N F, Douek D C, Barrett A J: In vitro induction of myeloid leukemia-specific CD4 and CD8 T cells by CD40 ligand-activated B cells gene modified to express primary granule proteins. *Clin. Cancer Res.* 11: 4495-4503, 2005

66. Coughlin C M, Vance B A, Grupp S A, Vonderheide R H: RNA-transfected CD40-activated B cells induce functional T-cell responses against viral and tumor antigen targets: implications for pediatric immunotherapy. *Blood* 103: 2046-2054, 2004

67. Sicard A, Koenig A, Morelon E, Defrance T, Thaunat O: Cell therapy to induce allograft tolerance: time to switch to plan B? *Front Immunol* 6: 149, 2015

68. Zheng J, Liu Y, Lau Y-L, Tu W: CD40-activated B cells are more potent than immature dendritic cells to induce and expand CD4(+) regulatory T cells. *Cell. Mol. Immunol.* 7: 44-50, 2010

69. Bovia F, Salmon P, Matthes T, Kvell K, Nguyen T H, Werner-Favre C, Barnet M, Nagy M, Leuba F, Arrighi J-F, Piguet V, Trono D, Zubler R H: Efficient transduction of primary human B lymphocytes and nondividing myeloma B cells with HIV-1-derived lentiviral vectors. *Blood* 101: 1727-1733, 2003

70. Janssens W, Chuah M K L, Naldini L, Follenzi A, Collen D, Saint-Remy J-M, VandenDriessche T: Efficiency of onco-retroviral and lentiviral gene transfer into primary mouse and human B-lymphocytes is pseudotype dependent. *Hum. Gene Ther.* 14: 263-276, 2003

71. Serafini M, Naldini L, Introna M: Molecular evidence of inefficient transduction of proliferating human B lymphocytes by VSV-pseudotyped HIV-1-derived lentivectors. *Virology* 325: 413-424, 2004

72. Bergwelt-Baildon von M, Shimabukuro-Vomhagen A, Popov A, Klein-Gonzalez N, Fiore F, Debey S, Draube A, Maecker B, Menezes I, Nadler L M, Schultze J L: CD40-activated B cells express full lymph node homing triad and induce T-cell chemotaxis: potential as cellular adjuvants. *Blood* 107: 2786-2789, 2006

REFERENCES

Throughout this application, various references describe the state of the art to which this invention pertains. The disclosures of these references are hereby incorporated by reference into the present disclosure.

The invention claimed is:

1. A nanoparticle, comprising a streptavidin coating and an amount of at least one antigen and an amount of at least one antibody having specificity for a human or mouse B cell receptor (BCR), wherein each of the at least one antigen and at least one antibody are attached to the surface of the nanoparticle via a linker having a biotin moiety and forming a streptavidin-biotin complex with the streptavidin coating, and wherein one of the at least one antigen is ovalbumin or a trimer HIV-GAG peptide, wherein the trimer HIV-GAG peptide has an amino acid sequence identity as set forth in SEQ ID NO:1.

2. The nanoparticle of claim 1 which is in the form of a sphere, made of an organic polymer and having a size in the range of 100 to 500 nanometers.

3. The nanoparticle of claim 1 wherein another antigen of the at least one antigen is viral antigen.

4. The nanoparticle of claim 1 wherein the at least one antigen is a HLA molecule.

5. The nanoparticle of claim 1 wherein the at least one antibody has specificity for the framework region of a kappa or lambda BCR light chain or for the framework region of a BCR heavy chain and is selected from the group consisting of rat anti-mouse kappa light chain (anti-κ mAb clone 187.1), mouse anti-human k light chain (clone G20-361), lambda light-chain (clone JC5-10) and human lambda light chain (clone JDC-12).

6. The nanoparticle of claim 1 wherein the at least one antibody comprises at least 2 or 3 anti-BCR antibodies, wherein each of said at least 2 or 3 anti-BCR antibodies is monobiotinylated and each monobiotinylated antibody is attached to the surface of the nanoparticle as part of a streptavidin-biotin complex.

7. The nanoparticle of claim 1, wherein the linker is a sulfo-NHS-LC-LC-biotin linker.

8. The nanoparticle of claim 2, wherein the sphere has a size in the range of 350-450 nanometers.

9. The nanoparticle of claim 2, wherein the sphere has a size of 400 nanometers.

10. The nanoparticle of claim 2, wherein the organic polymer comprises polystyrene.

11. The nanoparticle of claim 10, wherein the sphere has a size of 400 nanometers.

12. A nanoparticle able to be internalized by B cells, comprising
an organic polymer sphere having a size range of 100 to 500 nanometers;
a streptavidin coating;
a plurality of biotin linkers, wherein each biotin linker forms a streptavidin-biotin complex with the streptavidin coating;
at least one antigen capable of eliciting a T-cell response monobiotinylated to a first biotin linker; and
at least one antibody monobiotinylated to a second biotin linker, wherein said at least one antibody comprises specificity for the framework region of a mouse or human kappa or lambda B cell receptor (BCR) light chain or for the framework region of a mouse or human BCR heavy chain and is selected from the group consisting of rat anti-mouse kappa light chain(anti-κ mAb clone 187.1), mouse anti-human k light chain (clone G20-361), lambda light-chain (clone JC5-10) and human lambda light chain (clone JDC-12).

13. The nanoparticle of claim 12, wherein each of the plurality of biotin linkers is a sulfo-NHS-LC-LC-Biotin linker.

14. The nanoparticle of claim 12, wherein the organic polymer comprises polystyrene and the sphere has a size range of 350-450 nanometers.

15. The nanoparticle of claim 12, wherein the organic polymer comprises polystyrene and the sphere has a size of 400 nanometers.

16. The nanoparticle of claim 12, wherein said at least one antigen is selected from the group consisting of a protein, peptide nucleic acid, DNA plasmid, a tissue preparation and a cell preparation.

17. The nanoparticle of claim 12, wherein said at least one antigen comprises an antigen selected from the group consisting of a viral antigen, a bacterial antigen, a fungal antigen, a protozoal antigen, a tumor-associated antigen, an auto-antigen, an allergen, a xenoantigen, an alloantigen and an antigenic molecule that is exogenously administered for therapeutic or other purposes and may trigger an unwanted immune response.

18. The nanoparticle of claim 12, wherein said at least one antigen is ovalbumin or a triem HIV-GAG peptide, wherein the trimer HIV-GAG peptide has an amino acid sequence identity as set forth in SEQ ID NO: 1.

19. A nanoparticle, comprising
a polystyrene sphere having a size of 400 nanometers;
a streptavidin coating;
a plurality of sulfo-NHS-LC-LC-biotin linkers forming streptavidin-biotin complexes with said streptavidin coating;
an antigen, monobiotinylated to a first sulfo-NHS-LC-LC-biotin linker, wherein the antigen is ovalbumin or a trimer HIV-GAG peptide, wherein the trimer HIV-GAG peptide has an amino acid sequence as set forth in SEQ ID NO:1; and
an antibody, monobiotinylated to a second sulfo-NHS-LC-LC-biotin linker, wherein the antibody is specific for the framework region of a mouse or human kappa or lambda B cell receptor (BCR) light chain or for the framework region of a mouse or human BCR heavy chain and is selected from the group consisting of rat anti-mouse kappa light chain(anti-κ mAb clone 187.1), mouse anti-human k light chain (clone G20-361), lambda light-chain (clone JC5-10) and human lambda light chain (clone JDC-12);

wherein said nanoparticle is able to be internalized by B cells and is suitable for generating antigen-specific T cells.

* * * * *

SEQUENCE LISTING

```
<160> NUMBER OF SEQ ID NOS: 1

<210> SEQ ID NO 1
<211> LENGTH: 75
<212> TYPE: PRT
<213> ORGANISM: Artificial Sequence
<220> FEATURE:
<223> OTHER INFORMATION: Synthetic antigen

<400> SEQUENCE: 1

Ile Ile Leu Gly Leu Asn Lys Ile Val Arg Met Tyr Ser Pro Thr Ser
1               5                   10                  15
```

-continued

```
Ile Leu Asp Ile Arg Gln Gly Pro Lys Ile Ile Leu Gly Leu Asn Lys
            20                  25                  30

Ile Val Arg Met Tyr Ser Pro Thr Ser Ile Leu Asp Ile Arg Gln Gly
            35                  40                  45

Pro Lys Ile Ile Leu Gly Leu Asn Lys Ile Val Arg Met Tyr Ser Pro
        50                  55                  60

Thr Ser Ile Leu Asp Ile Arg Gln Gly Pro Lys
65                  70                  75
```